United States Patent
Potyrailo et al.

(10) Patent No.: US 6,360,585 B1
(45) Date of Patent: Mar. 26, 2002

(54) METHOD AND APPARATUS FOR DETERMINING CHEMICAL PROPERTIES

(75) Inventors: Radislav Alexandrovich Potyrailo, Niskayuna; Timothy Mark Sivavec, Clifton Park, both of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/519,895

(22) Filed: Mar. 6, 2000

(51) Int. Cl.$^7$ ................................................ G01N 27/00
(52) U.S. Cl. ...................................... 73/24.06; 422/83
(58) Field of Search .......................... 73/579, 597, 590, 73/24.01, 24.06; 310/340, 367, 369, 365, 311, 321; 422/83, 98

(56) References Cited

U.S. PATENT DOCUMENTS

| | | | |
|---|---|---|---|
| 3,327,519 A | | 6/1967 | Crawford |
| 4,255,964 A | * | 3/1981 | Morison ..................... 73/24.01 |
| 4,596,697 A | * | 6/1986 | Ballato ....................... 73/24.06 |
| 5,065,140 A | | 11/1991 | Neuburger ................. 73/23.31 |
| 5,076,094 A | | 12/1991 | Frye et al. .................. 73/24.04 |
| 5,201,215 A | | 4/1993 | Granstaff et al. ........... 73/54.41 |
| 5,369,033 A | | 11/1994 | Di Milia et al. ............ 73/24.04 |
| 5,411,709 A | | 5/1995 | Furuki et al. ................. 422/91 |
| 5,469,369 A | | 11/1995 | Rose-Pehrsson et al. ..... 73/23.2 |
| 5,616,827 A | | 4/1997 | Simmermon et al. ....... 73/29.01 |
| 5,852,229 A | * | 12/1998 | Josse et al. ................. 73/24.06 |
| 6,076,406 A | * | 6/2000 | Blair et al. .................... 73/590 |
| 6,222,366 B1 | * | 4/2001 | Dilger ........................ 73/24.06 |

FOREIGN PATENT DOCUMENTS

| | | |
|---|---|---|
| DE | 3220854 | 8/1981 |
| FR | 2629596 | 4/1988 |
| WO | 9102975 | 8/1992 |

OTHER PUBLICATIONS

Furuki, M.; Pu, L.S., Hybrid gas detector of squarylium dye Langmuir–Blodgett film deposited on a quartz oscillator, Thin Sold Films 1992, 210/211, 471–473.

Furuki M.; Pu, L.S., Gas detection by a multi–hydrid sensor with dye Langmuir–Blodgett films deposited on a quartz oscillator, Mol. Cryst. Liq. Cryst. 1993, 227, 325–337.

Hierlemann, A.; Ricco, A.J.; Bodenhöfer, K.; Göpel, W., Effective use of molecular recognition in gas sensing: results from acoustic wave and in situ FT–IR measurements, Anal. Chem. 1999, 3022–3035.

Thomas, R.C.; Hierlemann, A.; Staton, A.W.; Hill, M.; Ricco, A.J., Reflectance infrared spectroscopy on operating surface acoustic wave chemical sensors during exposure to gas–phase analytes, Anal. Chem.1999, 71, 3615–3621.

Rebière, D.; Bordieu, C.; Pistrè, J.; Improvement of surface acoustic wave gas sensor response time using neural–network pattern recognition; Elsevier Scienc S. A. 1995, pp 777–780.

Lucklum R.; Rösler S.; Hartmann J.; Hauptmann P.; On line detection of organic pollutants in water by thickness shear mode resonators; Elsevier Science S.A 1996; pp 103–111.

Carey W.P.; Beebe K. R.; Kowalski B.R.; Multicomponent analysis using an array of piezoelectric crystal sensor; Anal. Chem. 1987; PP. 1529–1534.

* cited by examiner

Primary Examiner—Helen Kwok
(74) Attorney, Agent, or Firm—Toan P. Vo; Norren C. Johnson

(57) ABSTRACT

A method and apparatus for determining chemical properties. The method is based on the sequential measurement of the variation of the oscillation frequency of a single sensing device when different chemically sensitive film materials are deposited on both sides of a resonator such as a quartz crystal microbalance (QCM). Each of the sides of the resonator is sequentially exposed to an analyte while another side is exposed to a blank gas. In this way, the analyte-dependent signal from the resonator is generated only from a single film. Measurements are further made by switching the analyte stream to expose the sensing film on another side of the resonator previously exposed to a blank.

20 Claims, 22 Drawing Sheets

METHOD AND APPARATUS FOR DETERMINING CHEMICAL PROPERTIES

BACKGROUND OF THE INVENTION

The invention relates to the identification and quantification of chemical properties. In particular, the invention relates to a method and apparatus for identifying and quantifying chemical species using transducers.

A number of analysis techniques are known by which various chemicals can be quantified and identified. For example coulometric, titrimetric, or calorimetric analyses techniques are known. Each of these techniques requires extended procedures that render near real-time and real-time measurements impractical. Infrared absorption spectroscopy and indirect chemiluminescence are known techniques having better response time. However, indirect chemiluminescence techniques have limited accuracy and infrared absorption spectroscopy techniques are relatively expensive to implement. Further, electrochemical transducers are well known for use in amperometric, coulometric, and potentiometric systems. However, such single transducers do not exhibit good chemical specificity, often require considerable maintenance and are particularly expensive. Other techniques rely upon significantly less expensive high temperature semiconductor transducers. However, these transducers also have a low chemical specificity and often have extremely demanding electrical power requirements.

It is known that a resonator, such as a piezoelectric quartz crystal, may be used as a chemical measurement transducer. Such transducers are generally more sensitive and selective and less expensive than other transducers. Resonators are inexpensive, readily available and can be coated with a compound, for example, a sensing film, responsive specifically to the presence of the chemical to be detected to control their chemical specificity. In particular, each resonator has a particular frequency of resonation when an electric potential is applied across it. As certain species are deposited in the surface of the resonator, the natural frequency of vibration changes. The changing frequency can be compared to that of a reference resonator not exposed to the chemical. The film can be used to permit specific species to pass therethrough to be deposited on the resonator surface. Accordingly, the transducer can be tuned to be responsive to various chemicals or chemical species in a known manner. However, the transducer response is not unique for each chemical or group of chemicals and thus known transducers based on resonators are not always accurate or even useful for all chemical species.

A single sensor may exhibit non-specific response in some sensing applications. Thus, identification and quantification of a target species may be adversely influenced. To overcome this possible adverse influence, arrays of sensors may be provided, in which at least one of the sensors in the array comprise a chemical sensor. Sensor arrays permit pattern recognition from the data collected that reflects the nature, property, and quantity of the target species. The number of sensors in a sensor array may vary; for example, the number may be two sensors to thousands of sensors, in which the number of sensors is usually dependent on various application criteria. These application include, but not limited to, type of desired sensor response, complexity of analyzed mixture, concentration of vapor or target species, signal levels produced by each sensor, noise levels produced by each sensor, similarity of response patterns, combinations thereof, and other sensor-related factors.

It is also known to reduce the number of transducers in transducer arrays by measuring plural parameters from a single sensing element. For example, U.S. Pat. No. 5,076, 094 discloses a method of identification and quantification of chemical species in which changes in both the velocity and the attenuation of an acoustic wave traveling through a thin film into which the chemical species is sorbed are measured. The dual output response provides two independent transducer responses from a single sensing device thereby providing twice as much information as a single output transducer and allowing a single transducer to provide both the concentration and the identity of a chemical species. It is also known to combine optical detection with acoustic wave measurements by coating an oscillating quartz crystal with a fluorescent dye and measuring both fluorescence intensity and the fundamental oscillation frequency as disclosed in U.S. Pat. No. 5,411,709.

Other types of optical spectroscopic measurements also have been combined with acoustic wave measurements. For example, it is known to combine surface acoustic wave (SAW) transducer measurements with direct in situ Fourier transform infrared external-reflectance spectroscopy as disclosed in Effective Use of Molecular Recognition in Gas Sensing; Hierlemann, A., Ricco, A. J., Bodenhofer, K. and Gopel, W.; Anal. Chem.; 1999,71, 3022–3035 and Reflectance Infrared Spectroscopy on Operating Surface Acoustic Wave Chemical Sensors During Exposure to Gas-Phase Analytes; Thomas, R. C., Hierlemann, A., Staton, A. W., Hill, M., and Ricco, A. J.; Anal. Chem.; 1999, 71, 3615–3621.

Finally, it is known to conduct simultaneous electrical conductivity and piezoelectric mass measurements on iodine-doped phthalocyanine Langmuir-Blodgett films to reduce the number of sensing elements by combining two measurement techniques on a single sensing element as disclosed in Simultaneous Electrical Conductivity and Piezoelectric Mass Measurements on Iodine-Doped Phthalocyanine Langmuir-Blodgett Films; Langmuir 1986, 2, 513–519.

Therefore, a need exists to provide enhanced apparatus for measurement of dual responses from a single sensing device that can provide more information compared to a single output transducer.

BRIEF SUMMARY OF THE INVENTION

A first aspect of the invention comprises an apparatus for determining chemical properties of an analyte. The apparatus comprises a vessel divided into plural compartments, a first resonator comprising a first side coated with a first sensing film and a second side coated with a second sensing film, the first side of the first resonator being exposed to a different one of the compartments than the second side of the first resonator. An electric power source is coupled to the first resonator and adapted to place an electric potential between the first side and the second side of the first resonator, and a frequency detector is coupled to the first resonator and adapted to detect the frequency of resonation of the first resonator.

A second aspect of the invention comprises a method for determining chemical composition. The method comprises a first step of exposing a first side of a first resonator coated with a first sensing film to an analyte and exposing a second side of the first resonator coated with a second sensing film to a blank, a first step of measuring the fundamental frequency of the resonator during the first step of exposing, a second exposing step comprising exposing the second side of the first resonator to the analyte and exposing the first side of the first resonator to the blank, a second step of measuring the fundamental frequency of the resonator during the second exposing step, and determining the chemical properties of the analyte based on the results of the first step of measuring and the second step of measuring.

A third aspect of the invention comprises an apparatus for determining chemical composition. The apparatus comprises first means for measuring the fundamental frequency of a first resonator while a first side of the first resonator coated with a first sensing film is exposed to an analyte and a second side of the first resonator coated with a second sensing film is exposed to a blank, second means for measuring the fundamental frequency of the resonator while the second side of the first resonator is exposed to the analyte and the first side of the first resonator is exposed to the blank, and means for determining the chemical properties of the analyte based on the results obtained by said first means for measuring and said second means for measuring.

A fourth aspect of the invention comprises an apparatus for determining chemical properties of an analyte. The apparatus comprises a vessel divided into plural compartments, a first quartz crystal microbalance resonator having a first side coated with a first sensing film and a second side coated with a second sensing film, the first side of the first quartz crystal microbalance resonator being exposed to a different one of the plural compartments than the second side of the first quartz crystal microbalance resonator, an electric power source coupled to the first quartz crystal microbalance resonator and adapted to place an electric potential between the first side and the second side of the first quartz crystal microbalance resonator, and a frequency detector coupled to the first resonator and adapted to detect the frequency of resonation of the first quartz crystal microbalance resonator.

BRIEF DESCRIPTION OF THE DRAWINGS

The invention will be described through the embodiments set forth herein and described in the drawing in which.

DETAILED DESCRIPTION OF THE INVENTION

Figure 1:
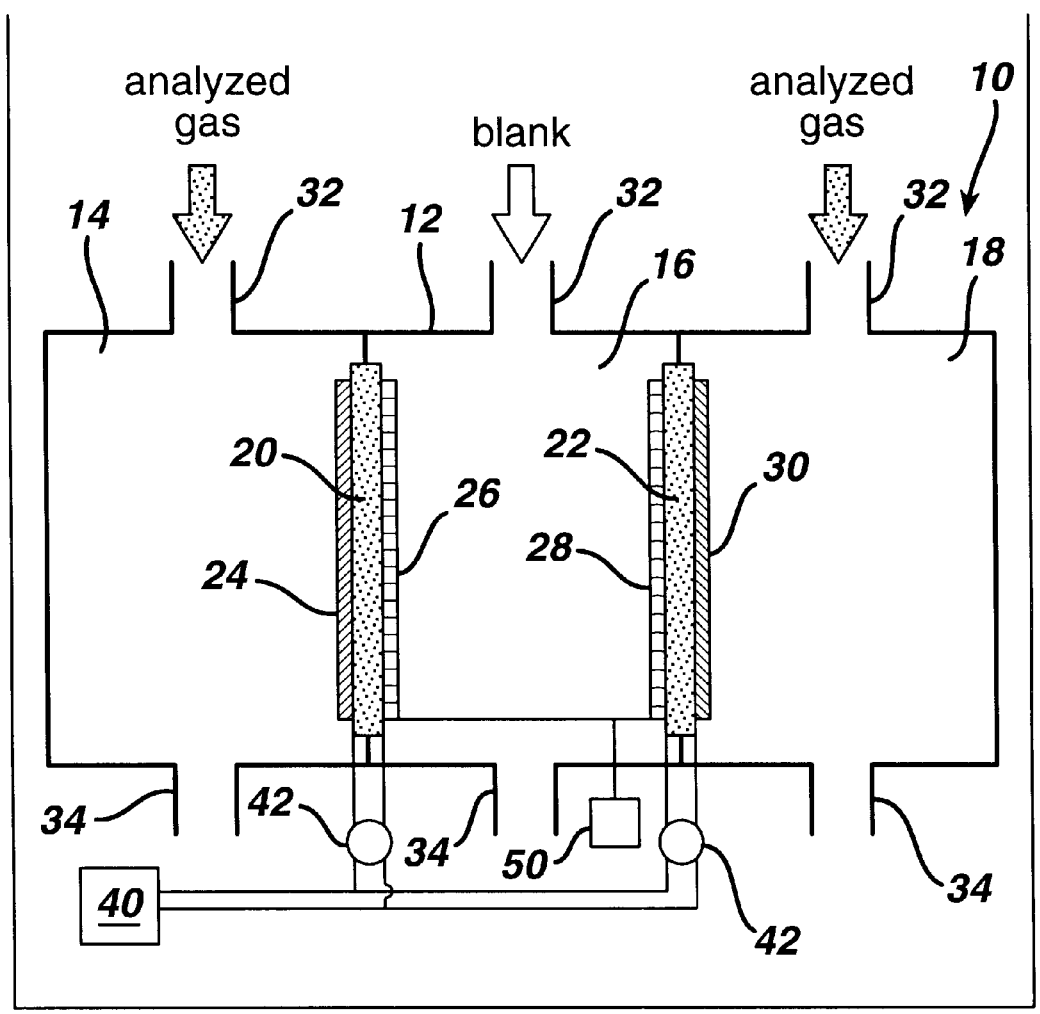
FIG. 1 is a schematic representation of a first embodiment in a first step of measuring with a transducer array.
Figure 2:
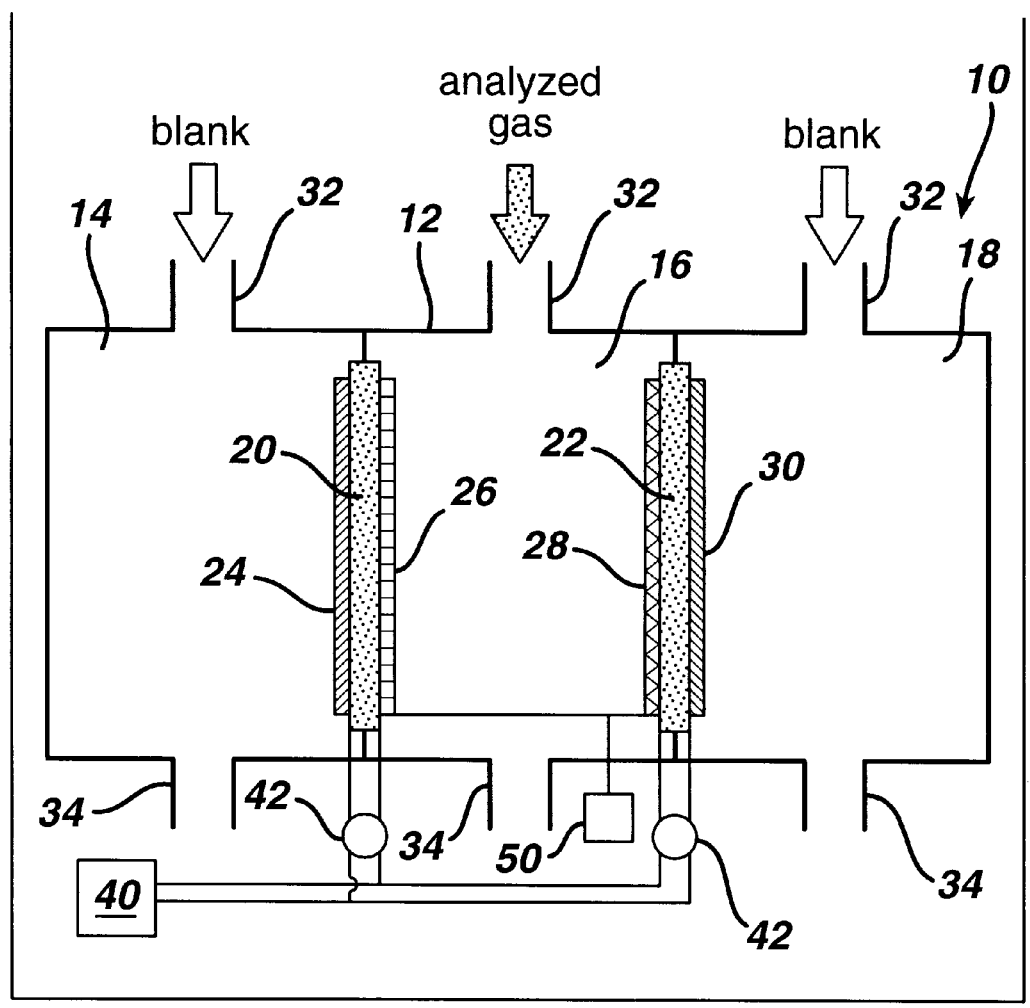
FIG. 2 is a schematic representation of the first embodiment in a second step of measuring with a transducer array.

FIGS. 1 and 2 illustrate a first, illustrative, and non-limiting embodiment of the invention. A chemical property measuring apparatus 10 comprises vessel 12 divided into three cells, for example, compartments that comprise at least a first compartment 14, second compartment 16, and third compartment 18. Resonators 20 and 22, which serve as transducers, are disposed in vessel 12. First and second resonators 20 and 22 may comprise quartz resonators, such as quartz crystal microbalance (QCM) devices. The resonators can comprise any type of device having vibration characteristics that vary based on the properties of a chemical in contact with the surface thereof. Resonators 20 and 22 respectively comprise portions of walls dividing vessel 12 into compartments 14, 16 and 18.

The resonator 20 comprises a first side that is exposed to compartment 14. The transducer film 24 is formed on the first side. The phrase "transducer film", as used herein, refers to any substance disposed on the resonators to render the resonators sensitive to a particular chemical substance, species of chemical, or other property of a chemical. The resonator 20 also comprises a second side exposed to compartment 16 and having transducer film 26 disposed thereon. Similarly, the resonator 22 comprises a first side that is exposed to compartment 16. The transducer film 28 is formed on the first side of resonator 22. The resonator 22 also comprises a second side exposed to compartment 18 with the transducer film 30 disposed thereon. Transducer films 24, 26, 28, and 30 can each comprise a different composition.

The transducer films 24, 26, 28, and 30 may comprise polymers containing softblocks and hardblocks. Thus, the films provide adequate adhesion to resonators 20 and 22 and desired sorption properties. Examples of these polymers comprise, but are not limited to, an amorphous fluoropolymer Teflon AF1600, a hard-soft block elastomer Siltem 2000, polyisobutylene (PIB), and polyepichlorohydrin (PECH).

An electric power supply 40, such as, but not limited to, a direct current (DC) voltage supply, can be coupled to oscillators 42, which respectively are coupled to resonators 20 and 22. Thus, an electric potential can be applied across the respective first and second surfaces of each resonator 20 and 22 for causing the resonators 20 and 22 to vibrate (also referred to as "to oscillate"). The electric power supply 40 and oscillators 42 comprise a power source. Only a schematic connection between power supply 40 and resonators 20 and 22 is illustrated. The connection can comprise known cabling and electrodes to place an electric potential across resonators 20 and 22.

A frequency detector 50 is coupled to resonators 20 and 22 to measure at least one of the frequency, phase, and magnitude of vibration in resonators 20 and 22. The frequency detector 50 can comprise any appropriate frequency detection device, such as, but not limited to, a solid state microprocessor based device. The frequency detector 50 can be coupled to resonators 20 and 22 in any appropriate manner. For example, and in no way limiting of the invention, strain gauge transducers, optical transducers or piezoelectric transducers can be used to detect oscillation of resonators 20 and 22.

Ports 32 and 34 can be provided with each compartment, 14, 16, and 18, to allow respectively the introduction and withdrawal of various chemical substances as described hereinafter to expose the substances to resonators 20 and 22. The ports 32 and 34 can comprise any type of valve and cover. Alternatively, the same port can be used for introduction and withdrawal of chemical substances.

A chemical measuring method using the first embodiment is described below. The analyzed fluid, such as a gas, is introduced into compartments 14 and 18 through port 32 and a blank, such as, but not limited to, a substance not containing the chemical substance or species to be quantified or detected, is introduced into compartment 16, as illustrated in FIG. 1. Accordingly, the analyte is exposed to films 24 and 30 and the blank is exposed to films 26 and 28. A predetermined voltage is applied across each resonator 20 and 22 by power supply 40 and oscillators 42 and the resulting oscillation frequency and/or magnitude is detected and recorded by oscillation detector 50. Subsequently, the fluids can be drained from each of compartments 14, 16, and 18 through orifices 34. Next, the blank is introduced into compartments 14 and 18 and the analyte fluid is introduced into compartment 16. Accordingly, films 26 and 28 can be exposed to the analyte and films 24 and 30 are exposed to the blank. Once again, a predetermined voltage can be applied across each resonator 20 and 22 by power supply 40 and the resulting oscillation frequency and magnitude is detected and recorded by oscillation detector 50. In this way, the analyte-dependent signal from each of resonators 18 and 20 is generated only from a single transducer film at a time and then switched to the other transducer film of the resonator. Applicant has applied various pattern recognition techniques of the measured oscillation of resonators 20 and 22 to quantify and identify , or detect other properties of the analyte in the fluid.

Figure 3:
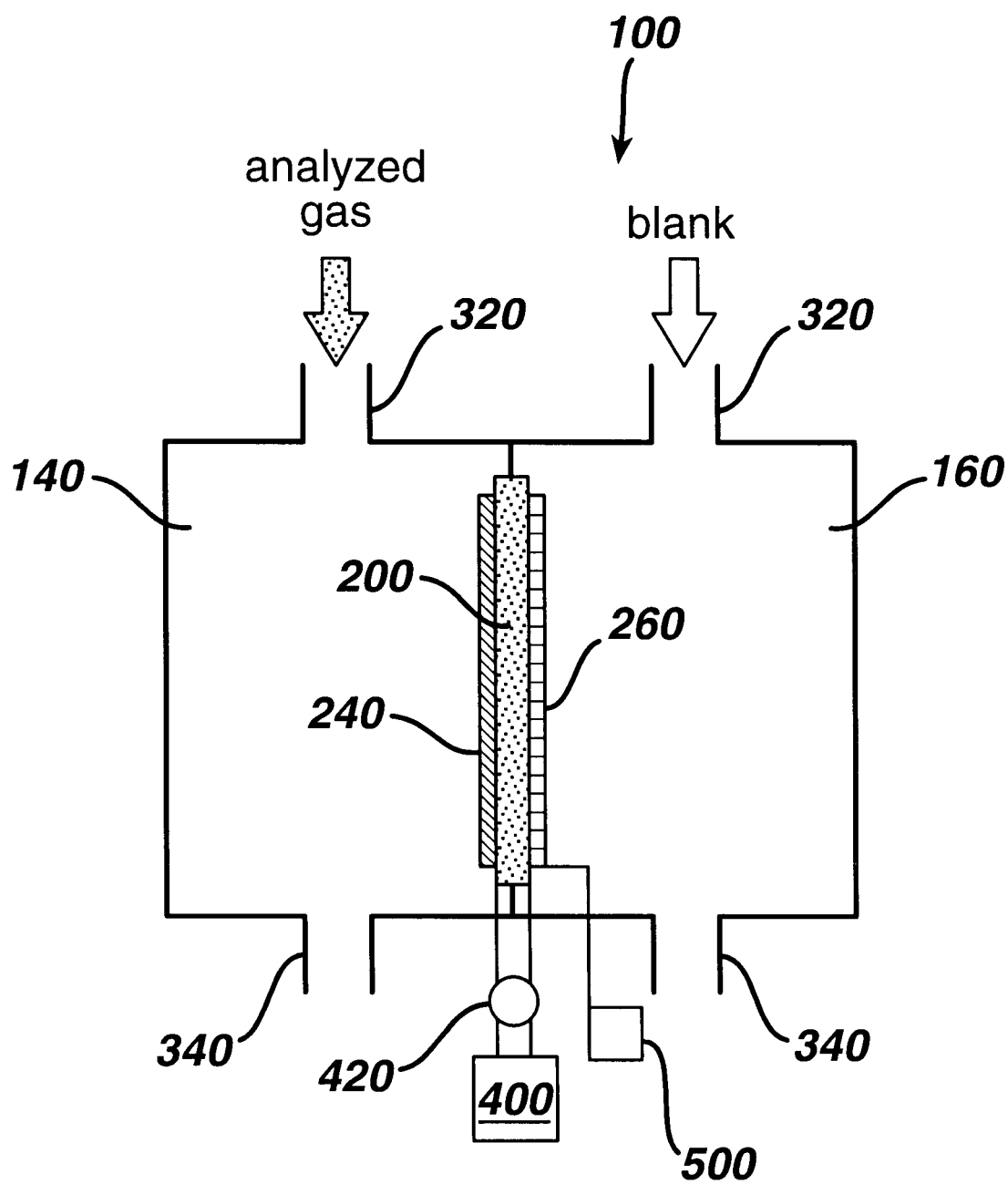
FIG. 3 is a schematic representation of a second embodiment having a single transducer in a first measurement step.
Figure 4:
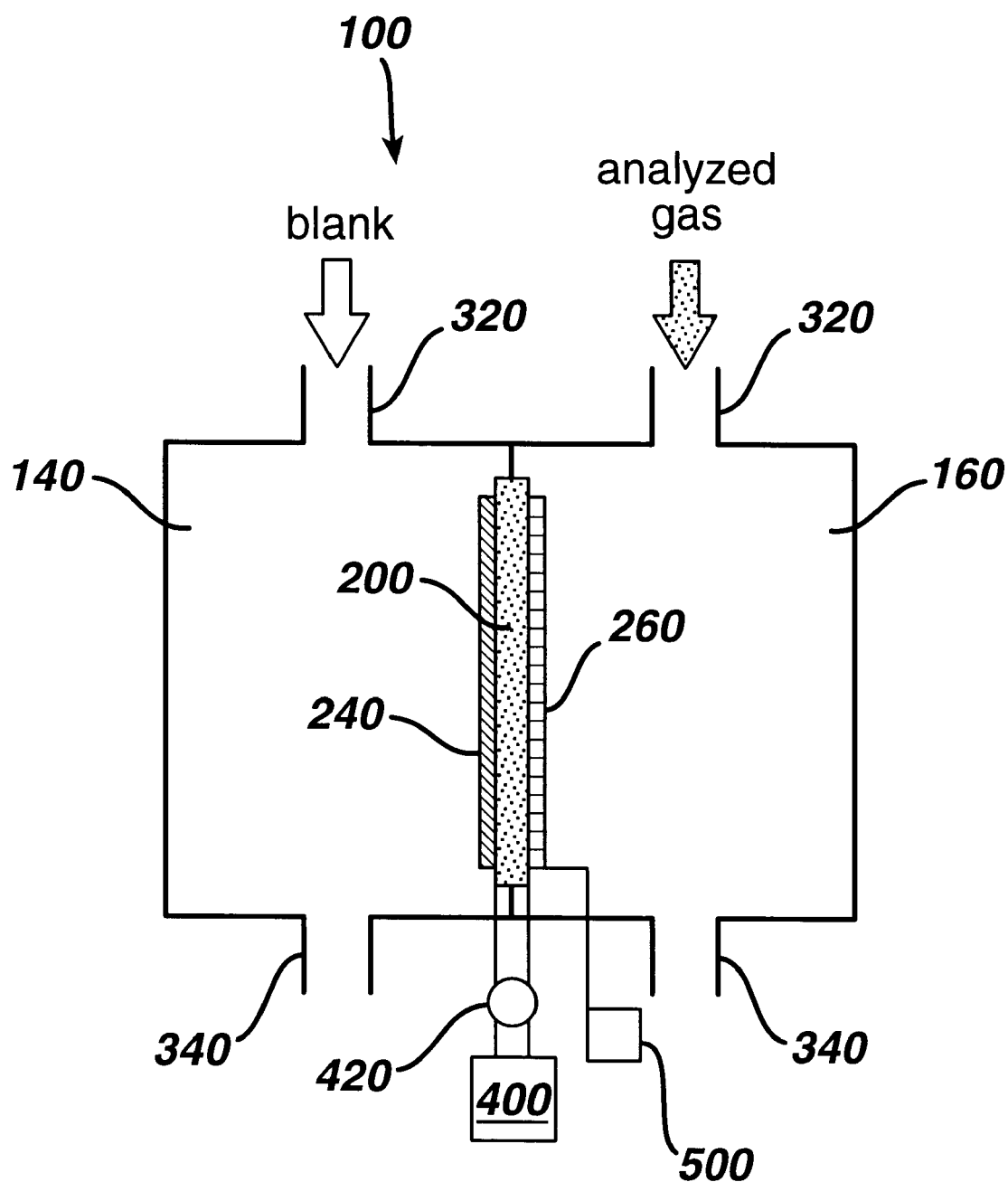
FIG. 4 is a schematic representation of the second embodiment in a second measurement step.

FIGS. 3 and 4 illustrate second, exemplary, and non-limiting embodiment in which chemical property measuring apparatus 100 can include a vessel 120 that is divided into two cells, a first compartment 140 and second compartment 160. Resonator 200 can be disposed in vessel 120. Resonator 200 of the second embodiment is a quartz resonator, such as a quartz crystal microbalance (QCM) device. However, the resonator can be any type of device having vibration characteristics that vary based on a chemical in contact with the surface thereof. Resonator 200 may define portions of a wall dividing vessel 120 into compartments 140 and 160.

Electric power supply 400, such as a DC voltage supply, can be coupled to oscillator 420. The oscillator 420 is coupled to resonator 200 to place an electric potential across the respective first and second surfaces of resonator 200. Thus, the resonator 200 can vibrate. Of course, the connection can use known cabling and electrodes to place an electric potential across resonator 200. Frequency detector 500 can be coupled to resonator 200 to measure at least one of the frequency and magnitude of vibration of resonator 200. The frequency detector 500 can be any appropriate type of known frequency detection device, such as, but not limited to, a solid state microprocessor based device. The frequency detector 500 can be coupled to resonator 200 through any appropriate mechanism. Ports 320 and 340 can be provided for each of compartments 140, 160 to allow the introduction and withdrawal of various chemical substances, as described below. Ports 320 and 340 can include any type of valve and cover.

Tests were conducted with an apparatus in accordance with the second embodiment. An AT-cut quartz crystal with gold electrodes is used as the substrate of resonator 200. An AT-cut quartz crystal typically oscillates in the thickness-shear mode with a fundamental frequency of 10 MHz. The crystal can be arranged in a low-dead volume flow-through two cell vessel. The resonant oscillation frequency of the resonator was monitored as a function of analyte concentration in a gas mixture. Analyte gas mixtures can be sequentially applied to each of the sides of the crystal, as described below.

Performance of the resonator was evaluated with respect to several analyte vapors such as toluene, trichloroethylene, and two isomers of dichloroethylene (DCE), cis-1,2-DCE, and trans-1,2-DCE. The vapors can be supplied at approximate concentrations of 105 ppm (toluene), 100 ppm (TCE), 101 ppm (cis-1,2-DCE), and 99 ppm (trans-1,2-DCE) in dry air. The vapors can be diluted with dry nitrogen generated various concentrations of vapors. The gas flow can be kept constant at about 480 $cm^3$/min using mass-flow controllers. The temperature of the transducer can be kept constant at about 20±0.1° C. The values set forth herein are approximate, unless otherwise specified.

EXAMPLE 1

The resonator described above is used for the quantification and discrimination of toluene and TCE. Each of the sides of the resonator can be coated with a different chemically sensitive polymeric film. The first side can be coated with polyisobutylene (PIB, Aldrich, average molecular weight 420,000). The second side of the crystal can be coated with an amorphous fluoropolymer (Teflon AF 1600, Du Pont, Inc.). For film deposition, PIB and amorphous fluoropolymer can be dissolved in chloroform and fluorinert (electronic liquid FC-75, 3M Company), respectively. Each polymer in solution, is applied to a single surface of the crystal and dried at room temperature for several hours. The thickness of the polymer films, measured as the shift of the fundamental oscillation frequency of the resonator, was about 52 and 36 kHz for PEB and amorphous fluoropolymer films, respectively.

Figure 5:
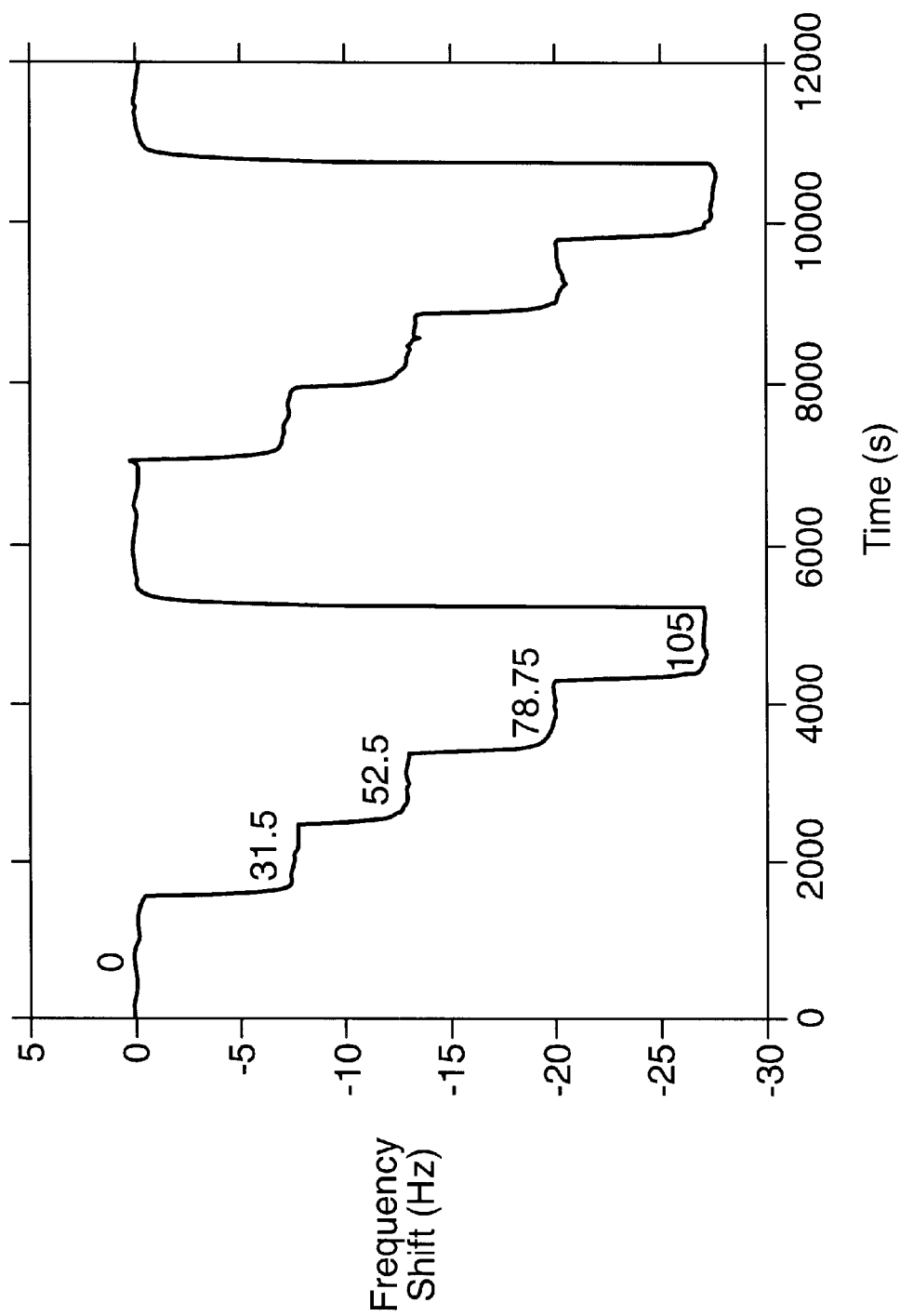
FIG. 5 is a graph of frequency shift versus time for increasing concentrations of toluene.
Figure 6:
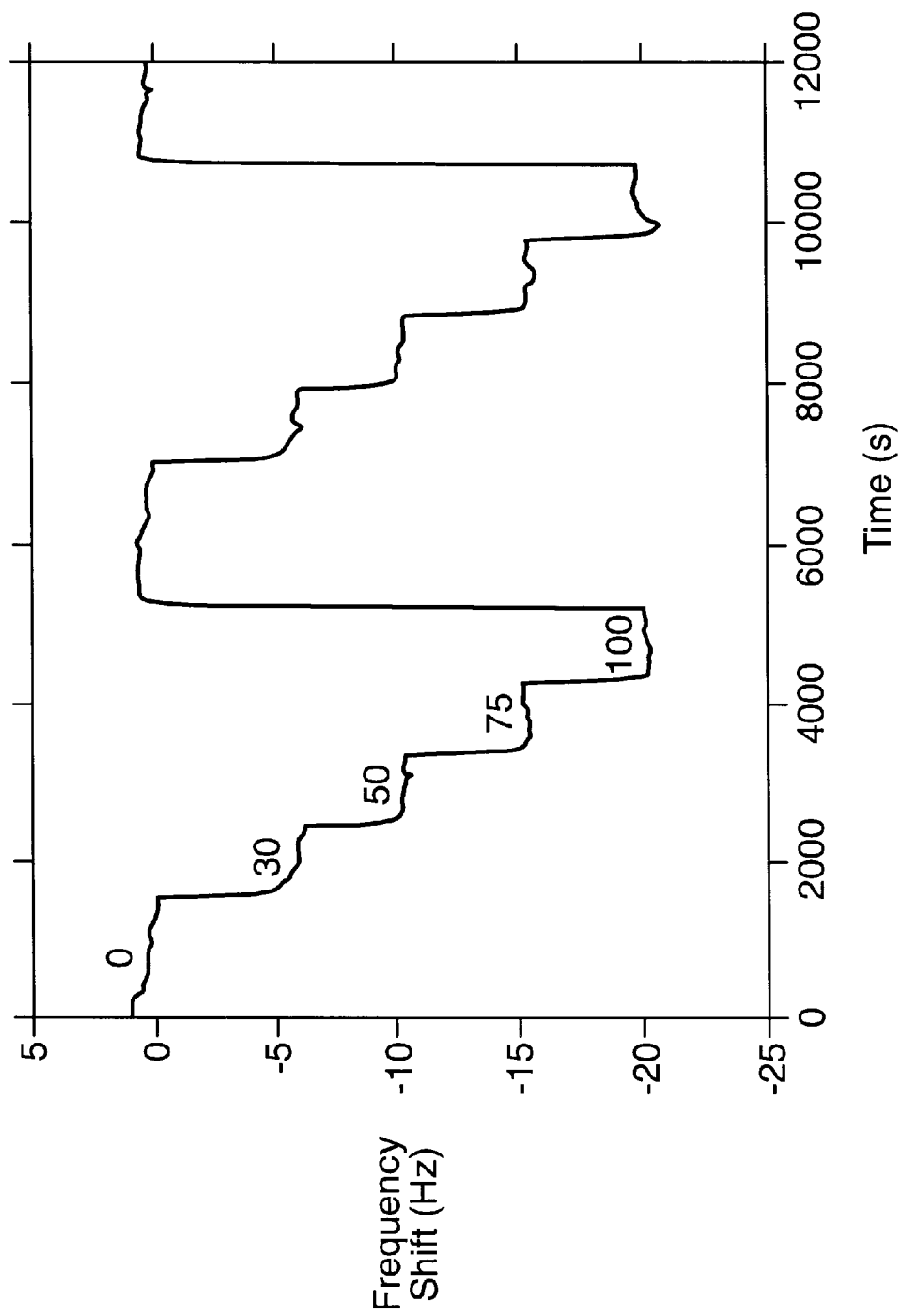
FIG. 6 is a graph of frequency shift versus time for various concentrations of TCE.
Figure 7:
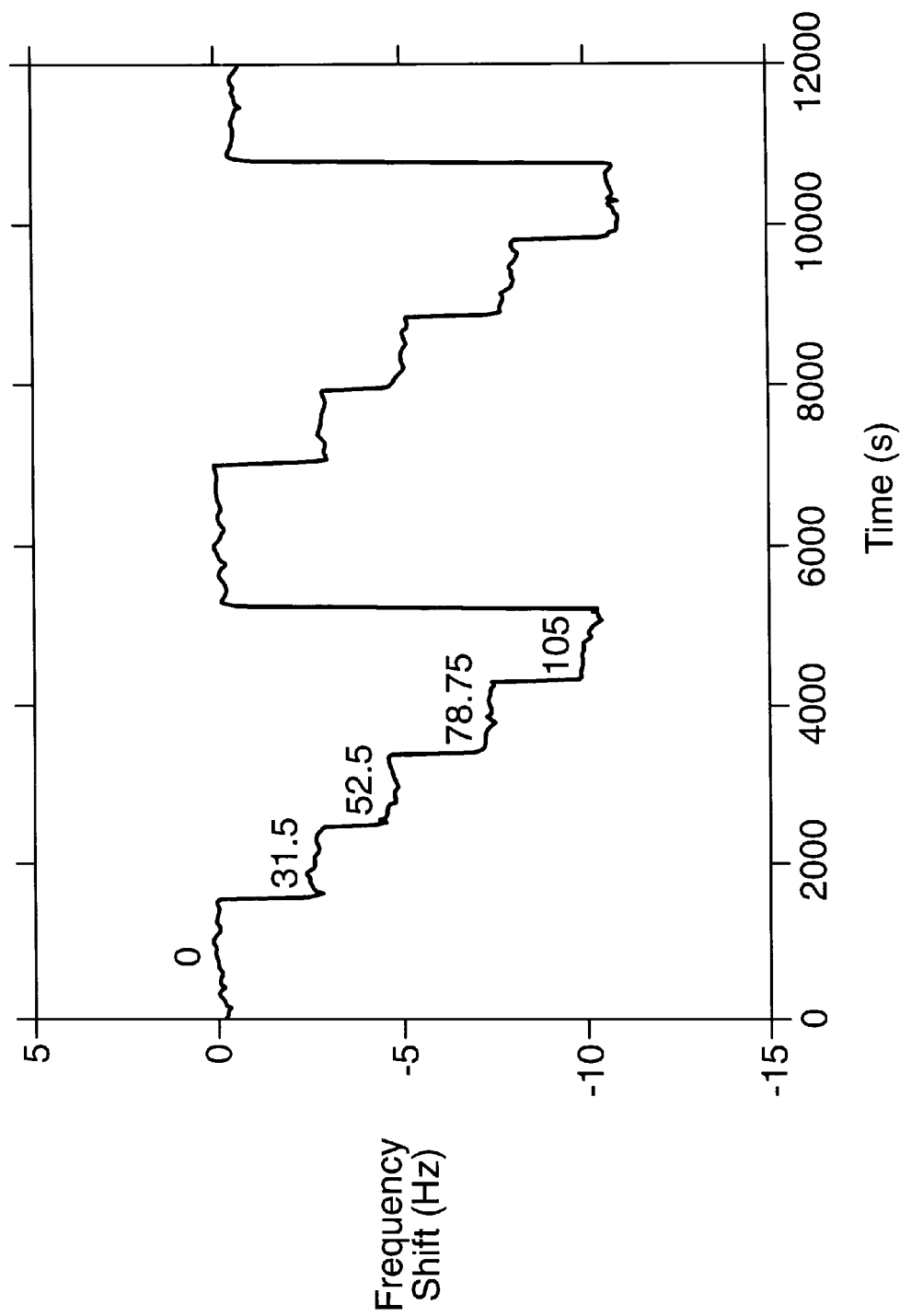
FIG. 7 is a graph of frequency shift versus time for various concentrations of toluene.
Figure 8:
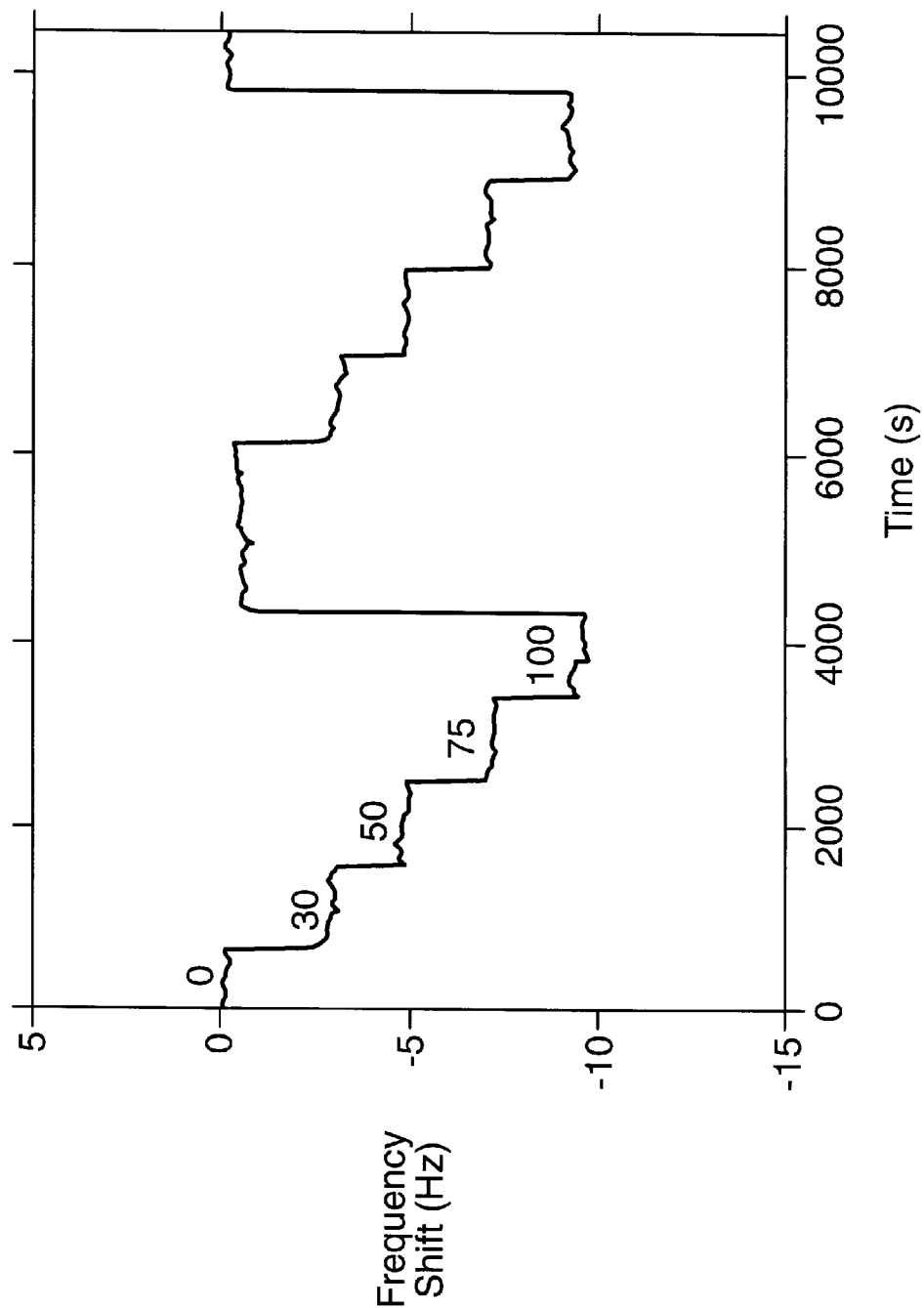
FIG. 8 is a graph of frequency shift versus time for various concentrations of TCE.

Upon exposure of the resonator to varying concentrations of toluene and TCE, the signal change, such as a change in measured oscillation, was recorded. The response of the resonator to the analyte vapors is determined to be essentially completely reversible. The dynamic response of the resonator is illustrated in FIGS. 5–8 in which the first and second sides are sequentially exposed to toluene and TCE vapors. The concentration range is varied over time from 0 to 102 ppm. FIG. 5 illustrates frequency shift for the PIB film exposed to toluene. FIG. 6 illustrates frequency shift for the PIB film exposed to TCE. FIG. 7 illustrates frequency shift for the amorphous fluoropolymer film exposed to toluene. FIG. 8 illustrates frequency shift for fluoropolymer film exposed to TCE. It can be seen that there is a step wire frequency shift at the concentrations (in ppm) indicated on the graphs of FIGS. 5–8.

Figure 9:
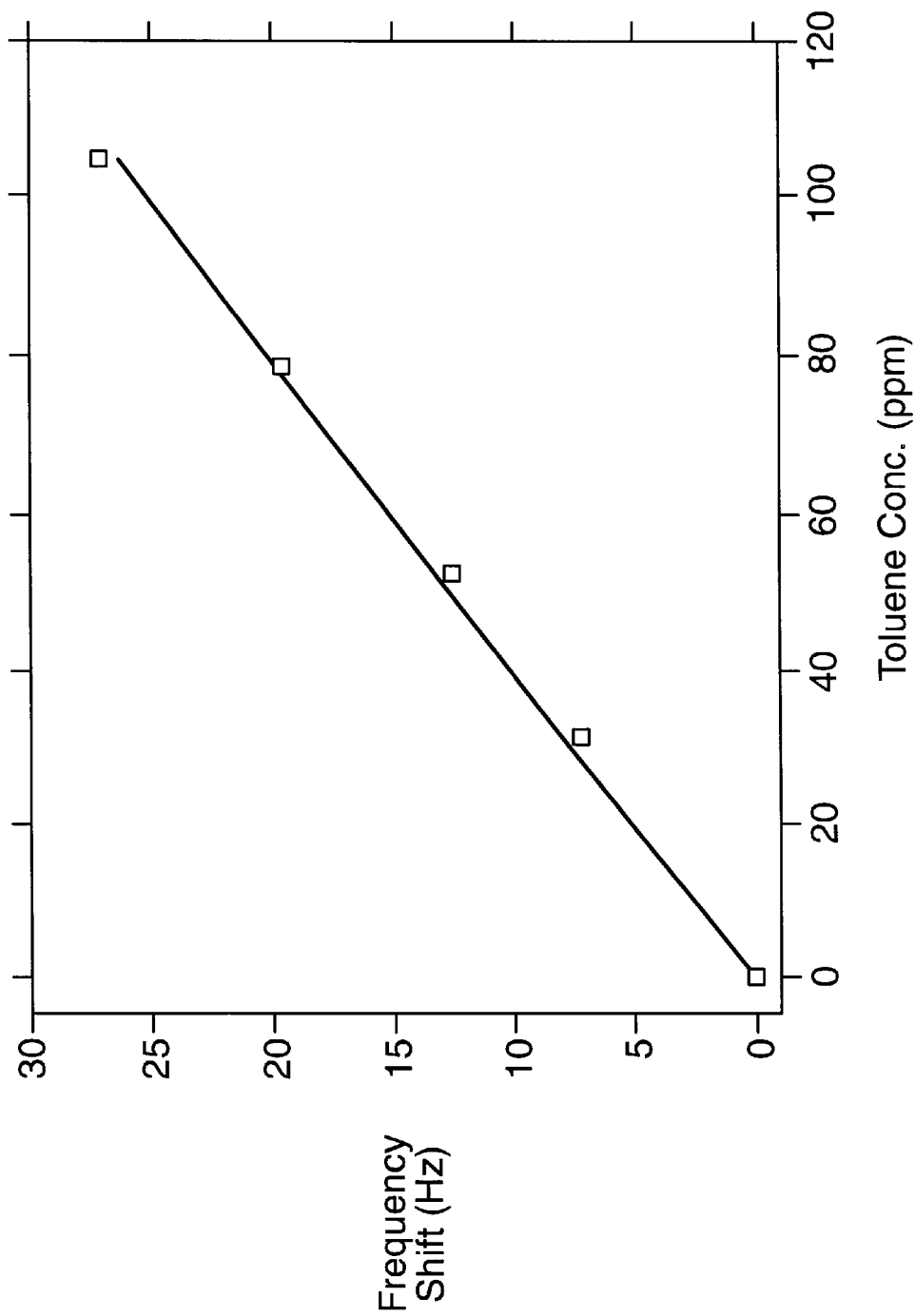
FIG. 9 is a graph of resonator frequency shift versus toluene concentration for the first film of Example 1.
Figure 10:
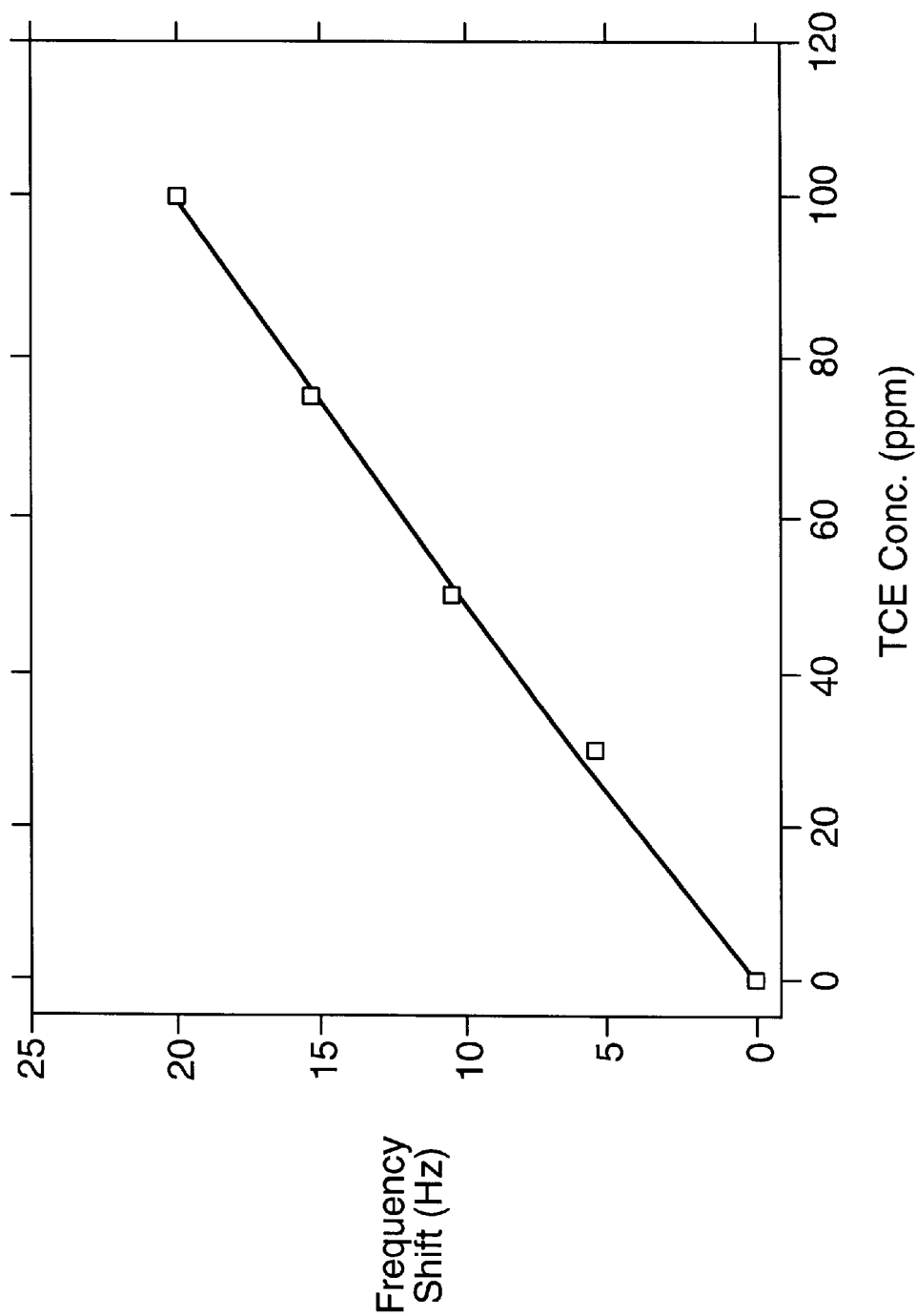
FIG. 10 is a graph of resonator frequency shift versus TCE concentration for the first film of Example 1.

Calibration curves for the resonator can be constructed by plotting the frequency change of the transducer as the function of analyte concentration. First, the first side of the transducer coated with the PIB film is exposed to analytes (toluene and TCE). The second side coated with an amorphous fluoropolymer is exposed to a blank gas. The change in fundamental oscillation frequency of the resonator with the PIB film exposed to toluene and an amorphous fluoropolymer film exposed to a blank is illustrated in FIG. 9. The change in fundamental oscillation frequency of the dual-response QCM with the PIB film exposed to TCE and an amorphous fluoropolymer film exposed to a blank is illustrated in FIG. 10.

Figure 11:
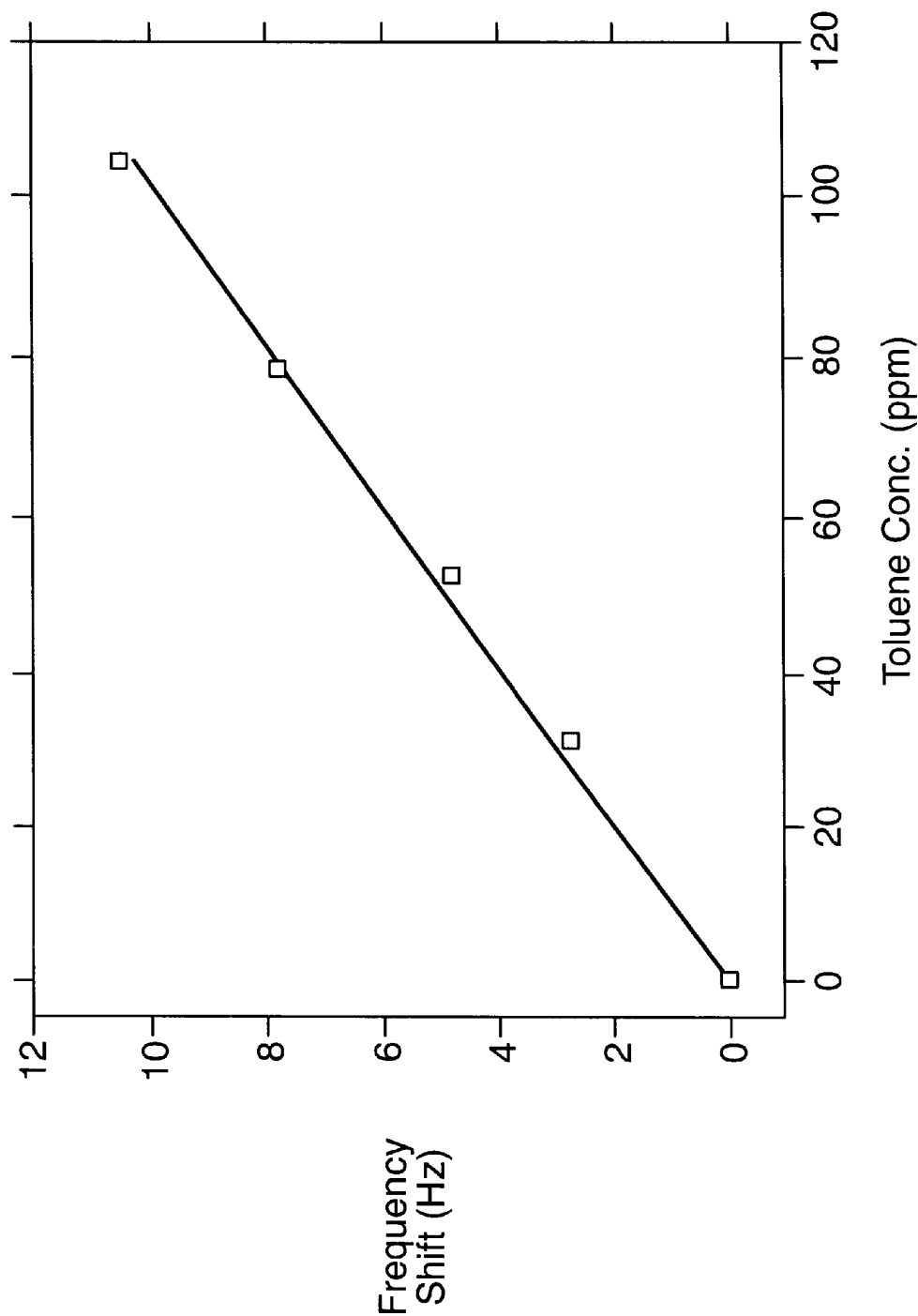
FIG. 11 is a graph of resonator frequency shift versus toluene concentration for the second film of Example 1.
Figure 12:
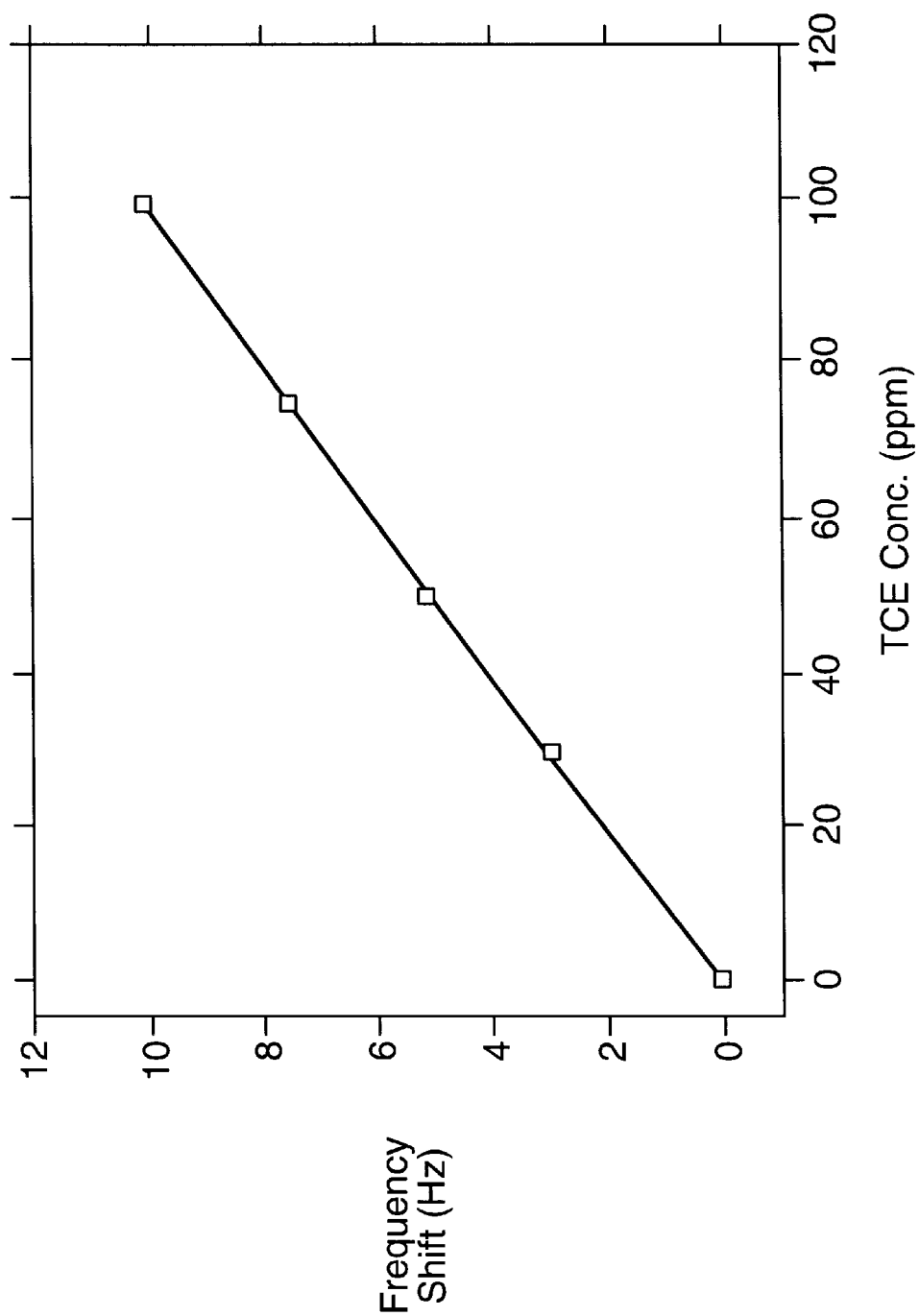
FIG. 12 is a graph of resonator frequency shift versus TCE concentration for the second film of Example 1.

Next, the second side of the resonator coated with the amorphous fluoropolymer film was exposed to toluene. The first side of the resonator coated with PIB was exposed to the blank gas. The resulting change in the fundamental oscillation frequency of the resonator is illustrated in FIG. 11. Similarly, the change in the fundamental oscillation frequency of the resonator with the amorphous fluoropolymer film (the second side) exposed to TCE and the PIB film (the first side) exposed to a blank is illustrated in FIG. 12.

Figure 13:
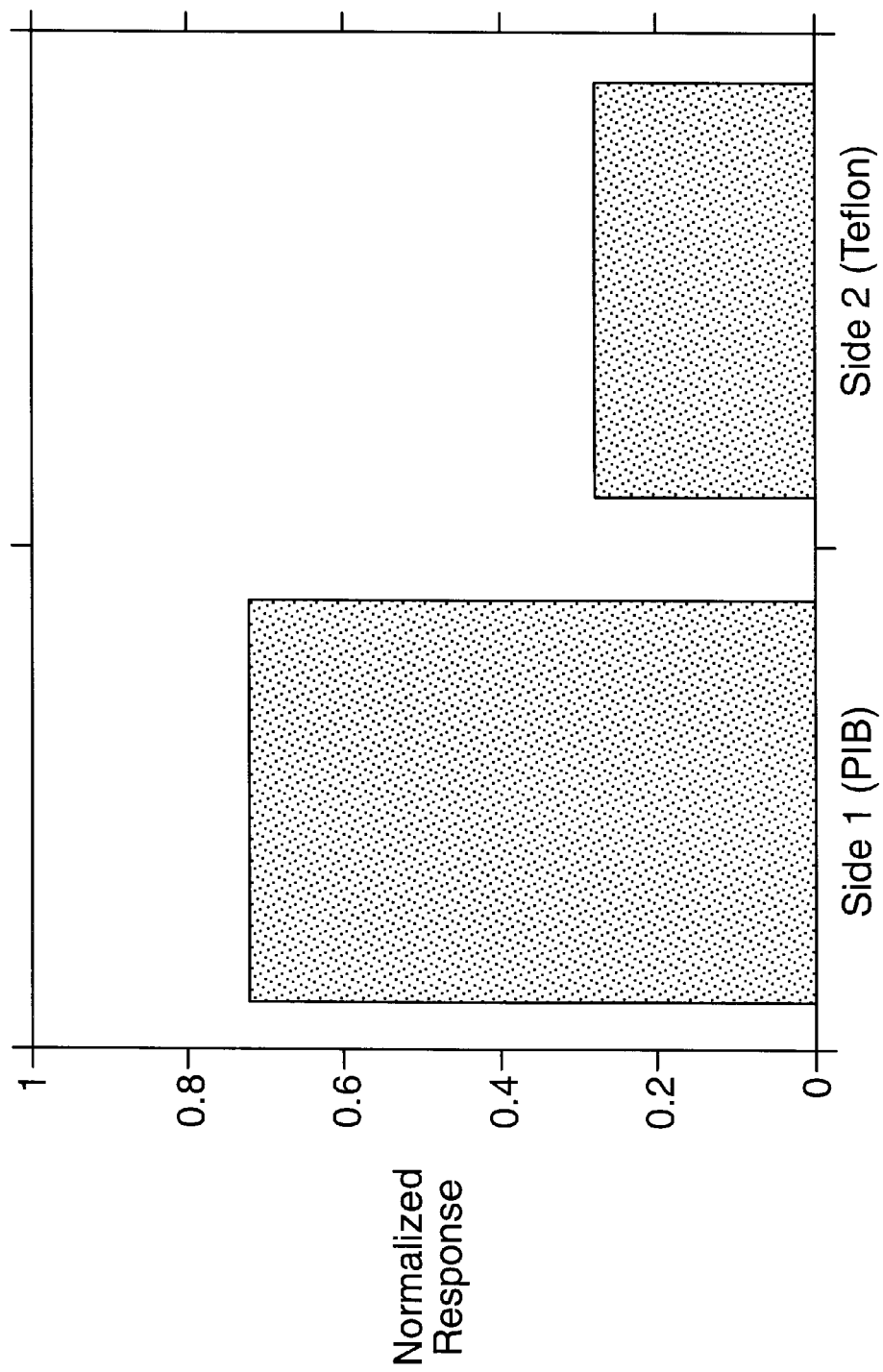
FIG. 13 is a graph of normalized responses of the first and second sides of the resonator toluene.
Figure 14:
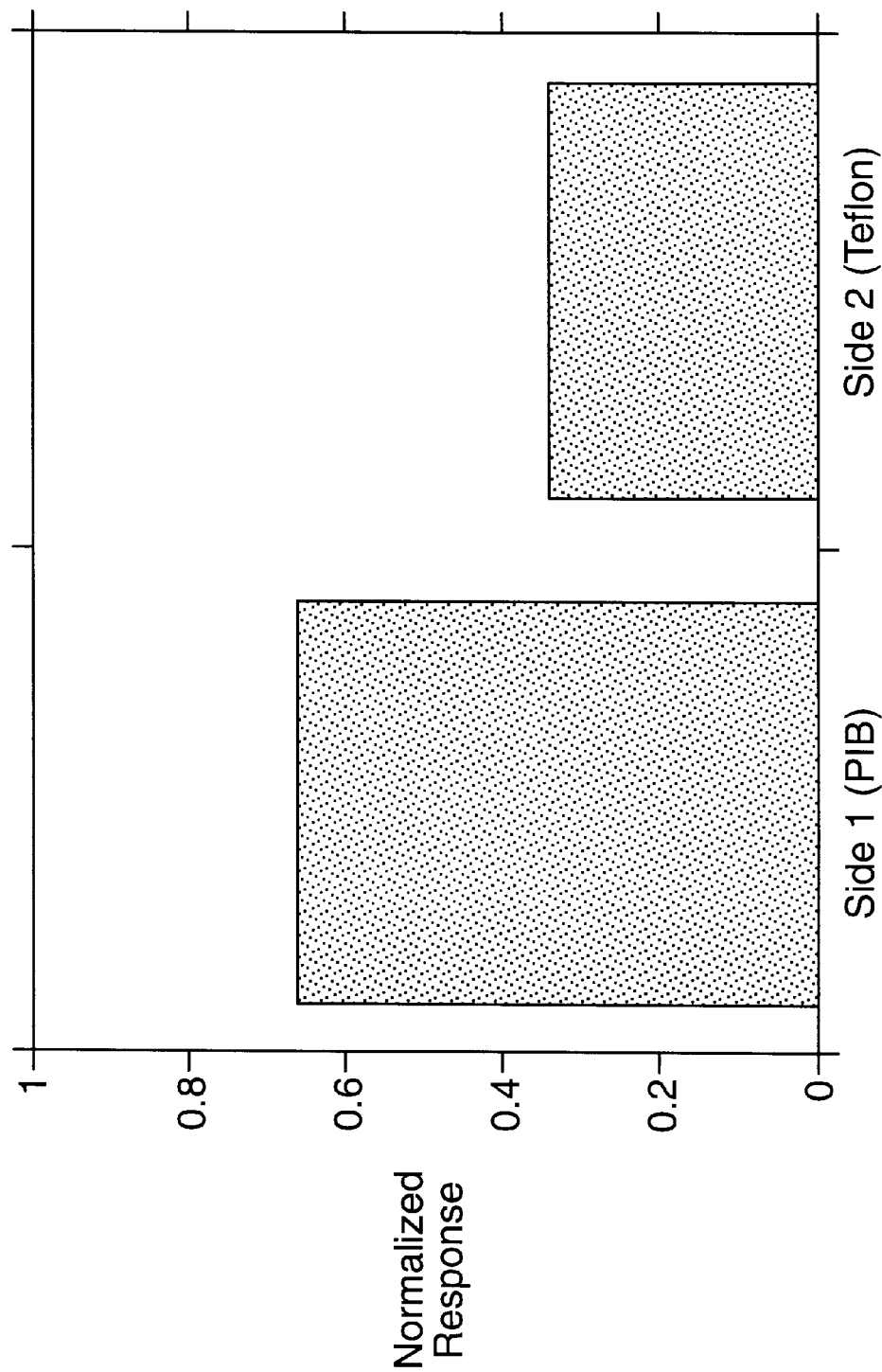
FIG. 14 is a graph of normalized response of the fist and second sides of the resonator to TCE.

The response patterns of the resonator to toluene and TCE were constructed to evaluate the capability of the resonator as a transducer to discriminate between different analytes. Normalized responses of the first and second sides of the resonator to toluene vapor are illustrated in FIG. 13. Normalized responses of the first and second sides of the resonator to TCE vapor are illustrated in FIG. 14. The normalized responses for the resonator for a particular vapor were determined by dividing the slope of the calibration curve for each individual chemically sensitive film by the sum of the slopes for both films. These response patterns illustrate the ability of the single resonator to recognize and differentiate vapors. In particular, the normalized response is a slope value for the response curve of the resonator side for the particular analyte. Accordingly, evaluation of the slope of the curve will indicate if a particular analyte or analytes are present.

Discrimination between different concentrations of toluene and TCE vapors was achieved by using known multivariate analysis, such as principal components analysis (PCA) techniques. When using PCA, data is rotated into a new set of axes, such that the first few axes reflect most of the variation of the data. The value of each point rotated to a give axis is called the "principal component value". The change in oscillation frequency due to varying concentrations of analyte was measured for each of the films three times for each of toluene and TCE. The analyte concentrations are indicated in FIGS. 5–8. The resulting frequency values were arranged in a 10×6 matrix (ten concentrations by three runs for each of two films).

Figure 15:
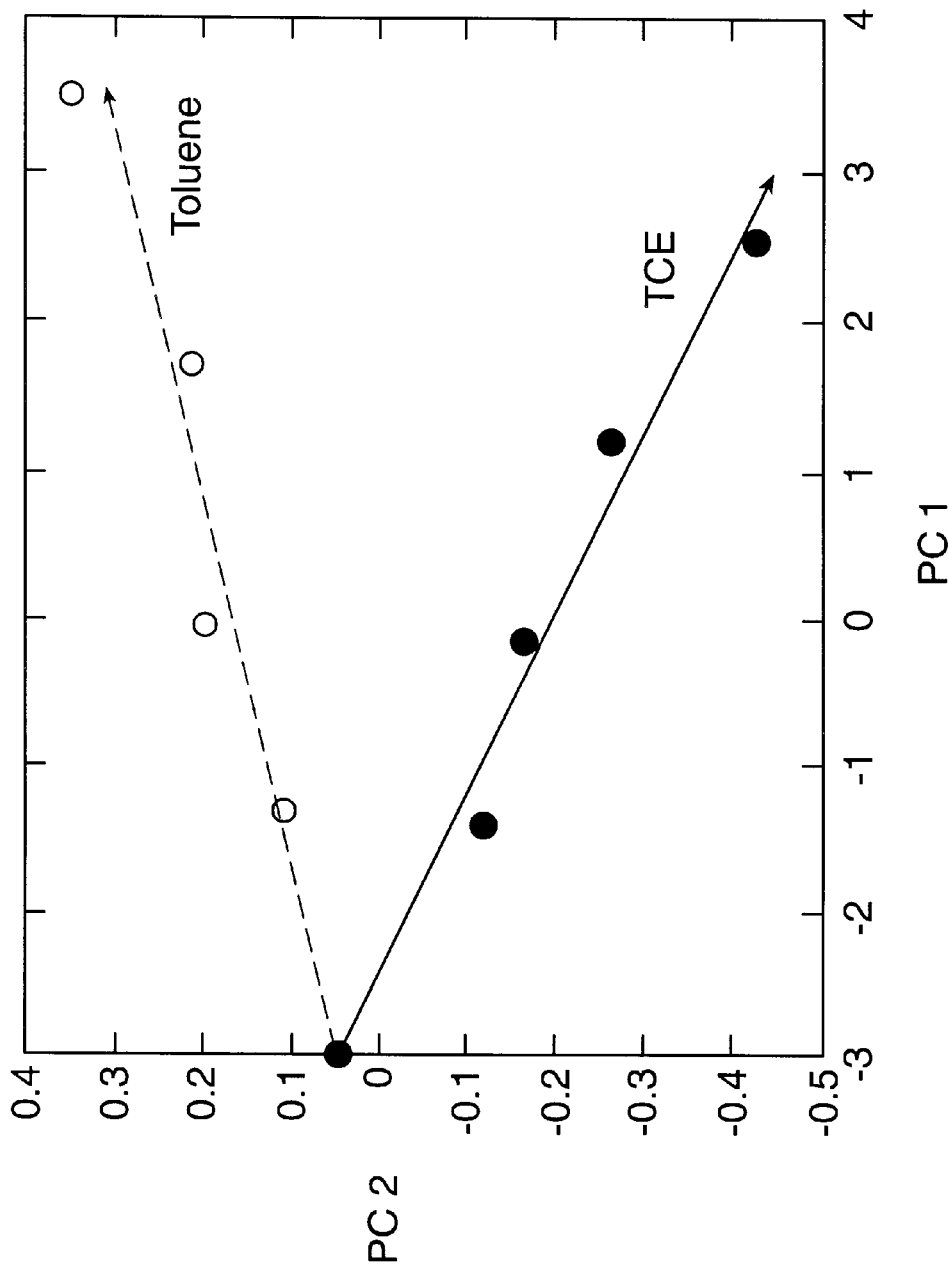
FIG. 15 is a graph of principal components analysis (PCA) of Example 1.

The matrix was analyzed using MATLAB software PLS Toolbox Edition™ principle components routine. The first two principal components were selected and plotted as axes in FIG. 15. FIG. 15 illustrates that the curves for toluene and TCE vapors are clearly separated from each other using PCA of the data set obtained from the responses of the first and second sides of the single crystal. The results illustrated in FIG. 15 demonstrate that with the increase in vapor concentration, the discrimination ability of the transducer also increases, as evidenced by a greater separation of the two curves.

EXAMPLE 2

A single resonator, such as that of the second embodiment is used for the quantification and discrimination of two isomers of DCE, trans-1,2-DCE and cis-1,2-DCE. Each of the sides of the resonator was coated with different chemically sensitive polymeric films. The first side of the resonator is coated with a hard-soft block elastomer (Siltem 2000, General Electric Co.). The second side of the crystal w as coated with polyepichlorohyrdin (PECH, Scientific Polymer Products, Inc. Ontario, N.Y.). For film deposition, the hard-soft block elastomer and PECH polymers can be dissolved in chloroform. The polymer solutions are applied to the proper surfaces of the crystal and dried at room temperature for several hours. The thickness of the polymer films, measured as the shift of the fundamental oscillation frequency of the crystal, is about 21 and about 38 kHz for the hard-soft block elastomer and PECH films, respectively.

Figure 16:
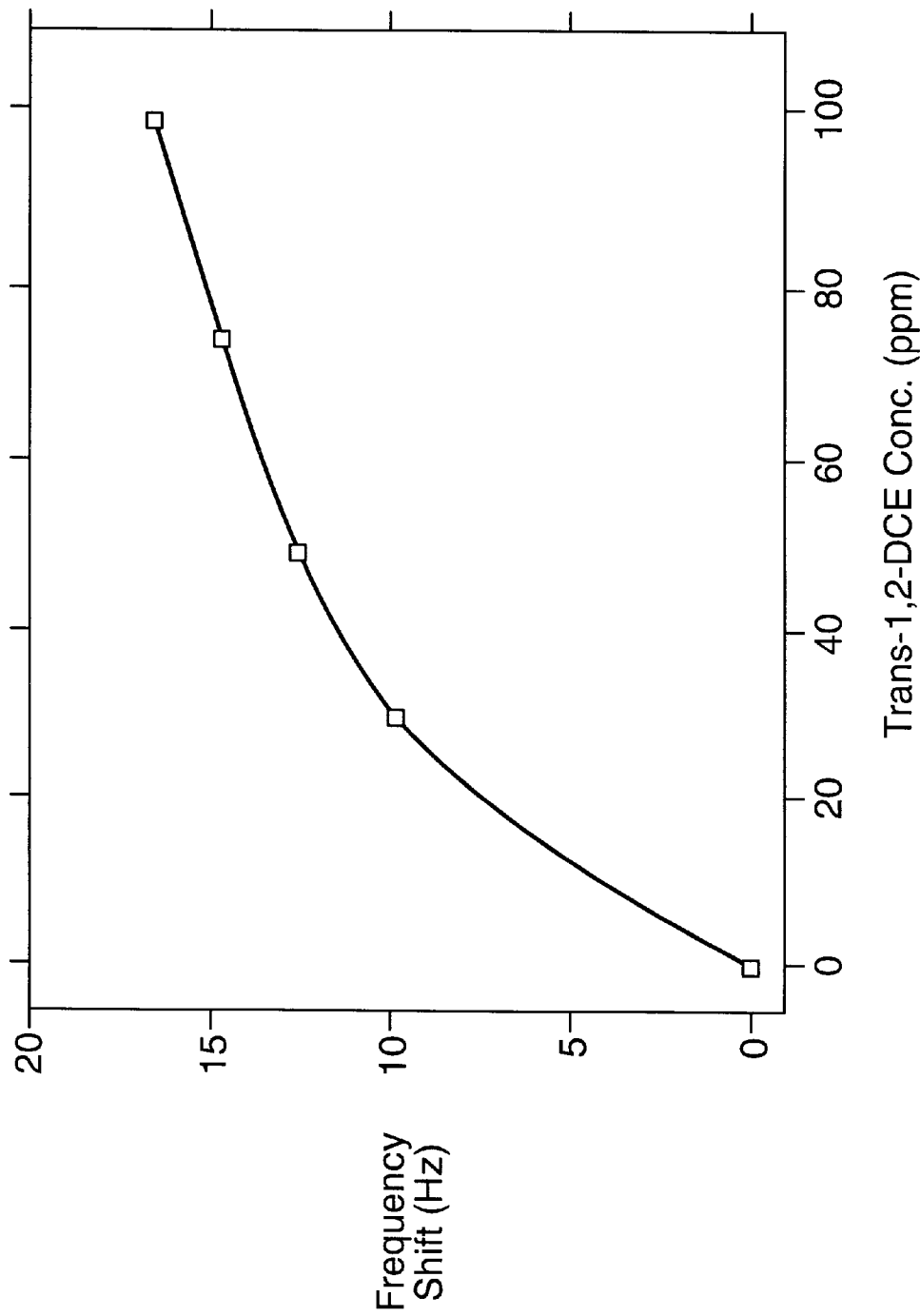
FIG. 16 is a graph of resonator frequency shift versus concentration of Trans-1,2 1-DCE concentration for the first film of Example 2.
Figure 17:
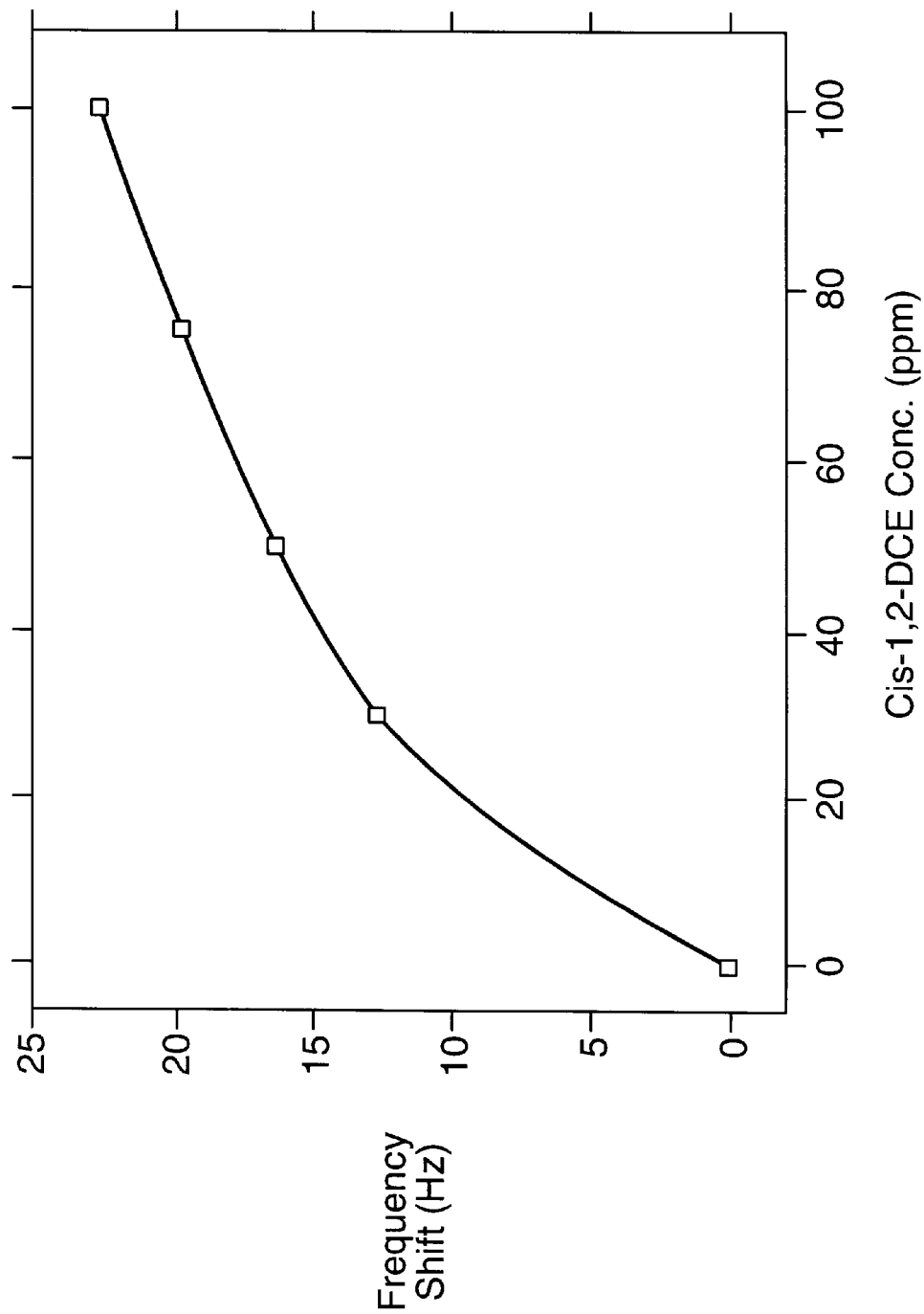
FIG. 17 is a graph of resonator frequency shift versus concentration of Cis-1,2-DCE concentration for the first film of Example 2.

Upon exposure of the resonator to varying concentrations of trans-1,2-DCE and cis-1,2-DCE, the signal change, such as fundamental frequency of oscillation, can be recorded. The calibration curves for the resonator were constructed by plotting the frequency change of the transducer as the function of analyte concentration. First, the first side of the resonator coated with the hard-soft block elastomer film was exposed to a respective one of the analytes (trans-1,2-DCE and cis-1,2-DCE). The second side coated with PECH film was exposed to the blank. The change in the fundamental oscillation frequency of the dual-response QCM with the hard-soft block elastomer film exposed to trans-1,2-DCE (first side) and PECH film (second side) exposed to a blank is illustrated in FIG. 16. The change in the fundamental oscillation frequency of resonator with the hard-soft block elastomer film exposed to cis-1,2-DCE and PECH film exposed to a blank gas is illustrated in FIG. 17.

Figure 18:
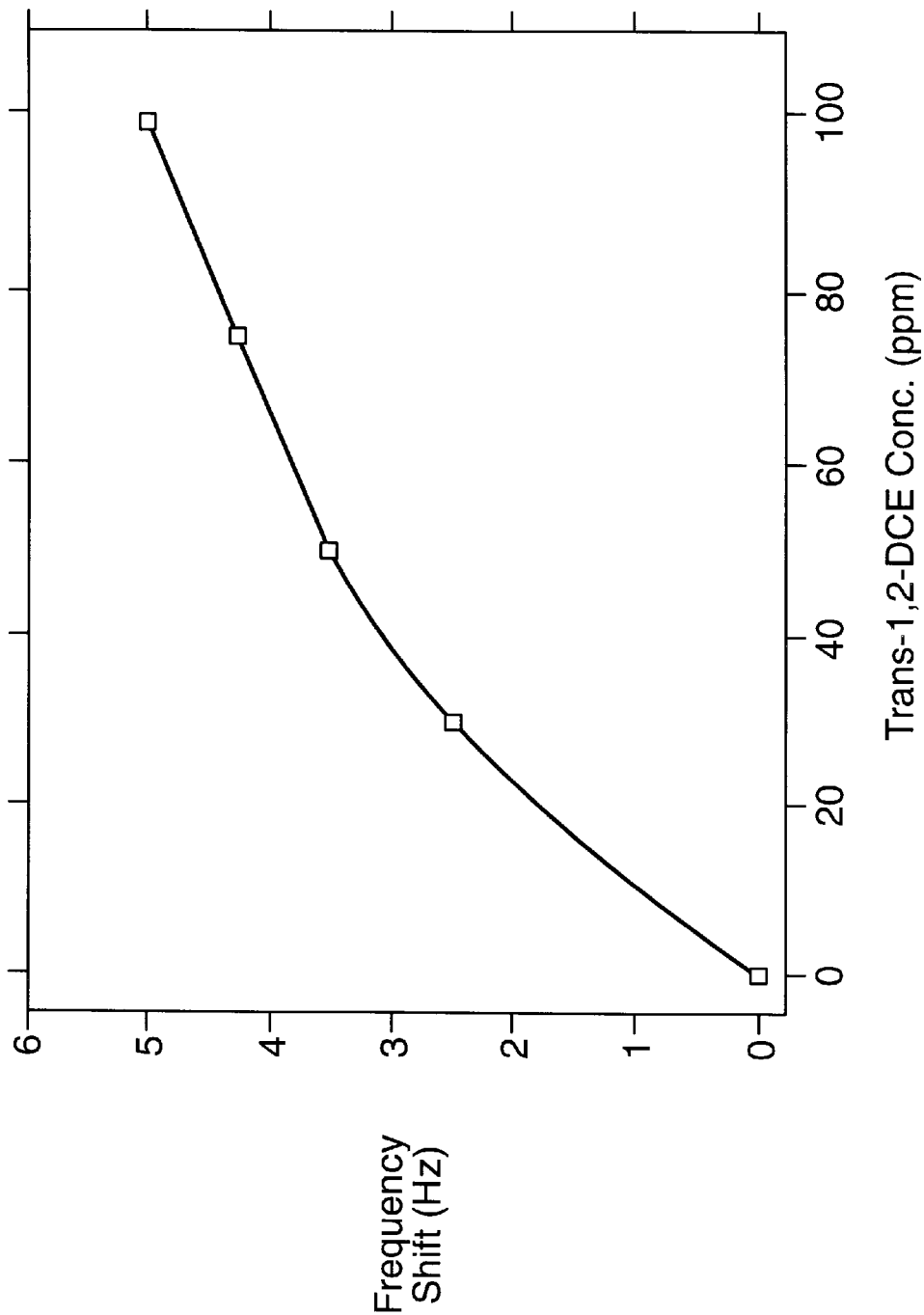
FIG. 18 is a graph of resonator frequency shift versus concentration of Trans-1,2-DCE concentration for the second film of Example 2.
Figure 19:
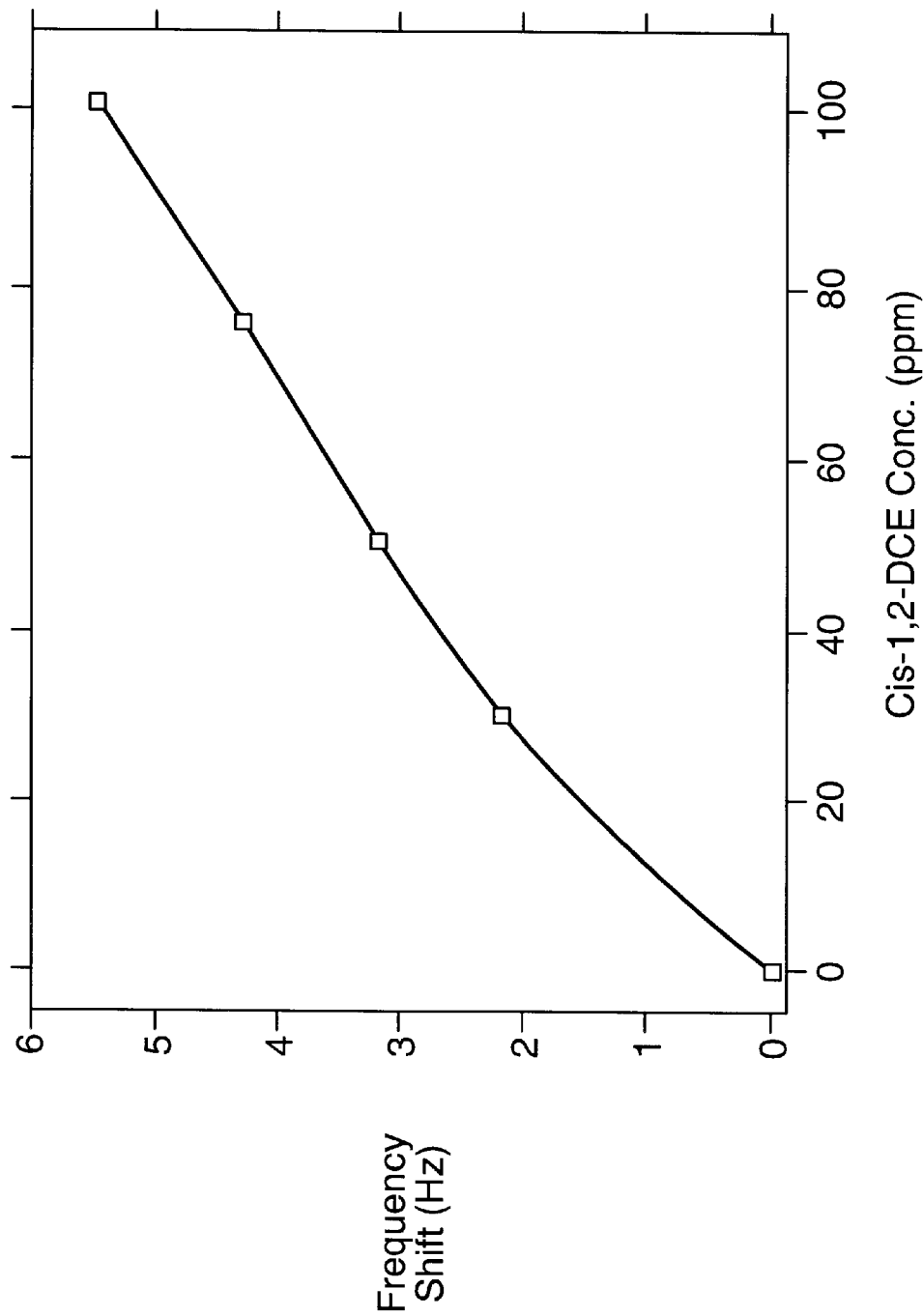
FIG. 19 is a graph of resonator frequency shift versus concentration of Cis-1,2-DCE concenit ration for the second film of Example 2.

Next, the second side of the resonator coated with PECH film is exposed to a respective one of the analytes (trans-1, 2-DCE and cis-1,2-DCE). The first side coated with the hard-soft block elastomer was exposed to the blank. The change in the fundamental oscillation frequency of the resonator QCM with the PECH film being exposed to trans-1,2-DCE and the hard- soft block elastomer film being exposed to a blank is illustrated in FIG. 18. The change in fundamental oscillation frequency of the dual-response QCM with PECH film exposed to cis-1,2-DCE and the hard-soft block elastomer film exposed to a blank is illustrated in FIG. 19.

Figure 20:
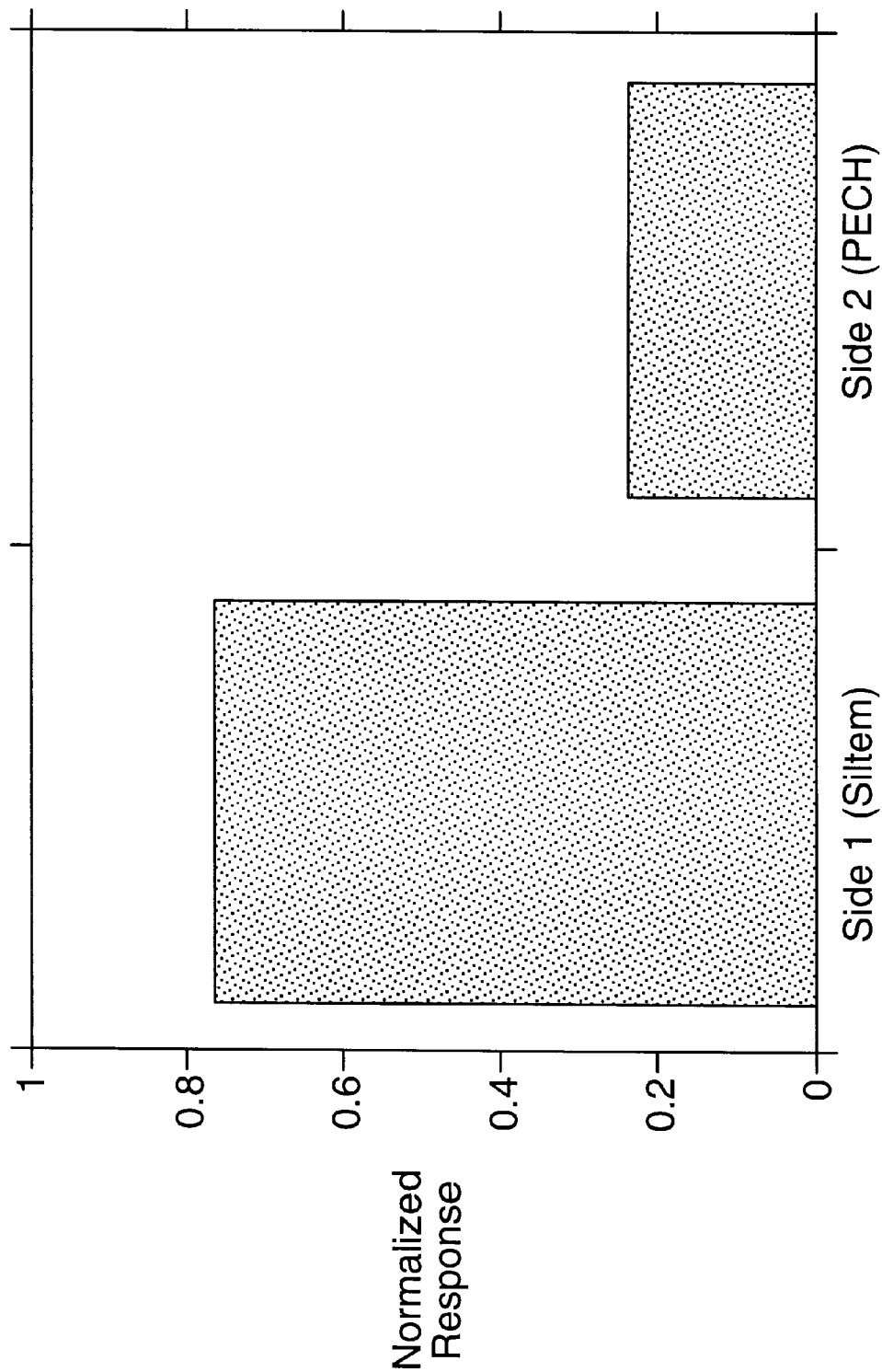
FIG. 20 is a graph of normalized response of the first and second sides of the resonator to Trans-1,2-DCE.
Figure 21:
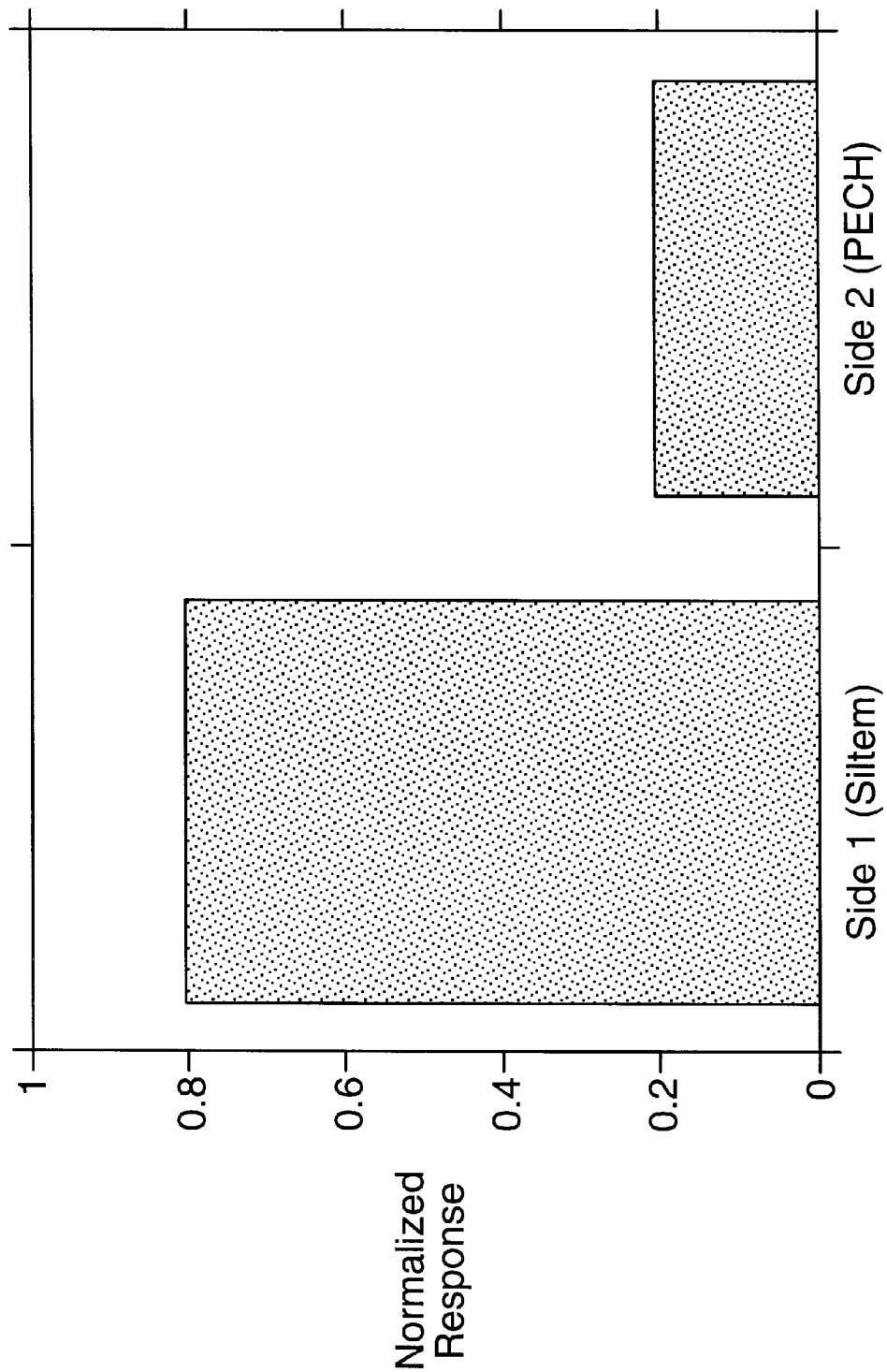
FIG. 21 is a graph of normalized response of the first and second sides of the resonator to Cis-1,2-DCE.

The response patterns of the resonator to trans-1,2-DCE and cis-1,2-DCE can be constructed to evaluate the capability of the resonator to discriminate between two isomers of DCE. Normalized responses of the first and second sides of the resonator to trans-1,2-DCE vapor are illustrated in FIG. 20. Normalized responses of the first and second sides of the resonator to cis-1,2-DCE vapor are illustrated in FIG. 21. These normalized responses are determined by dividing the slope of the calibration curve for each individual chemically sensitive film by the sum of the slopes for both films. These response patterns illustrate the ability of the single crystal to recognize and differentiate closely related vapors, such as DCE isomers.

Figure 22:
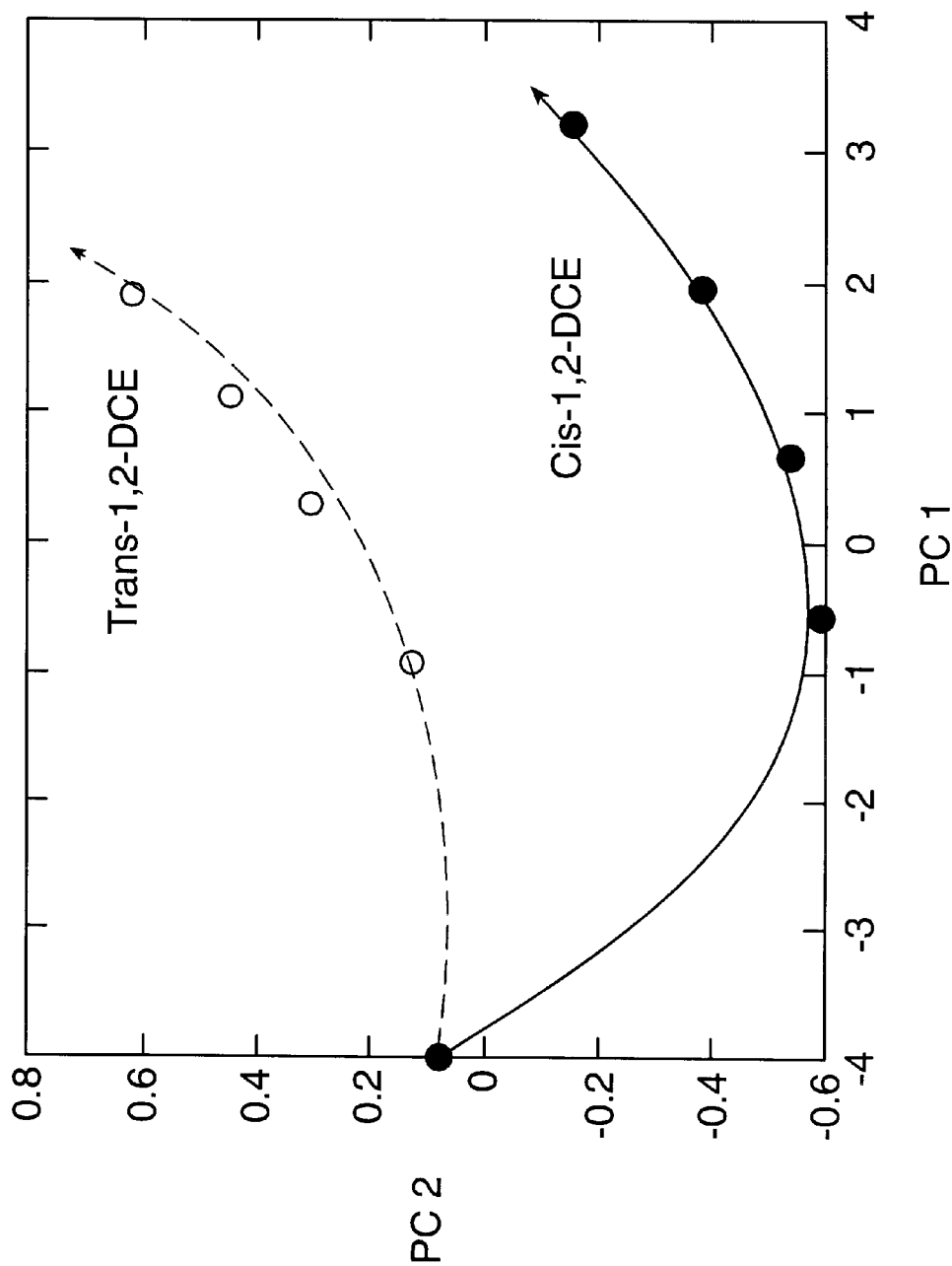
FIG. 22 is a graph of principal components analysis (PCA) of Example 2.

Discrimination between different concentrations of trans-1,2-DCE and cis-1,2-DCE vapors can be achieved by using multivariate analysis, such as principal components analysis (PCA). The test results illustrated in FIG. 22 illustrate that the curves for trans-1,2-DCE and cis-1,2-DCE vapors are clearly separated from each other using PCA of the data set obtained from the responses of the first and second sides of the single crystal. FIG. 22 demonstrates that with the increase in vapor concentration, the discrimination ability of the transducer increases. The graph of FIG. 22 was achieved in a manner similar to FIG. 15.

Thus, the invention provides enhanced information content from a single sensor, such as a resonator for identification and quantification of chemical species. The method of detection can be based on the sequential measurement of the variation of the oscillation frequency of a single sensing device if different chemically sensitive films are deposited on both sides of a piezoelectric transducer such as a quartz crystal microbalance (QCM). The increase of the information content can be achieved by utilizing each side of the sensing element independently, for example by sequentially exposing each side to an analyzed substance, while the other side is exposed to a blank. In this way, the analyte-dependent signal from the QCM can be generated only from a single film. Measurements can be done by switching the analyte stream to be exposed to a sensing film on the other side of the QCM previously exposed to a blank.

Any type and number of transducers can be used in the apparatus, as embodied by the invention. Any appropriate coatings can be used on the transducers, as embodied by the invention. Further, any type of analyte can be detected by the apparatus, as embodied by the invention, such as, but not limited to, a gas or a liquid. The geometric arrangement of the test apparatus can be modified in accordance with the practical considerations of the measurement procedure to be accomplished. The vessel can include any number of compartments and can be sealed or open. Therefore, the term "vessel" as used herein can refer to any mechanism for introducing the analyte to the transducer, such as, but not limited to, a container, a tube, a conduit, or even an open area having a concentration of the analyte therein. Various types of instrumentation can be used to measure the transducer response. The method can include any number of steps of measuring transducer response conducted in any order. The various calculations can be accomplished manually, by a preprogrammed computer, or in any other manner using various algorithms.

The invention has been described through embodiments and examples. However, various modifications can be made without departing from the scope of the invention as defined by the appended claims and legal equivalents thereof.

What is claimed is:

1. An apparatus for determining chemical properties of at least one chemical species in a sample of an analyte, the apparatus comprising:

a vessel divided into a plurality of compartments;

at least one resonator comprising a first side coated with a first sensing film comprising a first material and a second side coated with a second sensing film comprising a second material different than said first material, each of said sides of said at least one resonator being exposed to a different one of said plurality of compartments, each of said first and second materials having a respective differentiable affinity toward said at least one chemical species and being capable of inducing a respective differentiable resonant frequency in said at least one resonator upon contact with said at least one chemical species, one of said materials contacting said sample of said analyte when another of said materials contacting a reference chemical, and each of said materials contacting said sample of said analyte at a different time;

an electric power source coupled to said at least one resonator and adapted to place an oscillating electric potential between said first side and said second side of said at least one resonator; and a frequency detector coupled to said at least one resonator and adapted to detect the frequency of resonation of said at least one resonator;

wherein said at least one resonator generates differing resonant frequencies when each of said materials contacts said sample of said analyte, respectively; and said differing resonant frequencies provide a determination of said chemical properties of said at least one chemical species.

2. An apparatus according to claim 1, wherein said vessel comprises at least first and second compartments and wherein said first side of said at least one resonator is exposed to said first compartment and said second side of said at least one resonator is exposed to said second compartment.

3. An apparatus according to claim 2, wherein said first sensing film and said second sensing film comprise different chemical compositions.

4. An apparatus according to claim 3, wherein said at least one resonator comprises at least one quartz crystal microbalance resonator.

5. An apparatus according to claim 4, the apparatus further comprising a first wall disposed in said vessel to divide said vessel into a first compartment and a second compartment, said at least one quartz crystal microbalance resonator comprising at least a portion of said first wall.

6. An apparatus according to claim 4, wherein said at least one quartz crystal microbalance resonator comprises an AT-cut quartz crystal substrate that comprises a first side coated with PIB and a second side coated with an amorphous fluoropolymer.

7. An apparatus according to claim 4, wherein said at least one quartz crystal microbalance resonator comprises an AT-cut quartz crystal substrate that comprises a first side coated with a hard-soft block elastomer and a second side coated with PECH.

8. An apparatus according to claim 3, further comprising a second resonator that comprises a first side coated with a third sensing film and a second side coated with a fourth sensing film.

9. An apparatus according to claim 8, wherein said vessel is divided into first, second, and third compartments and said first side of said second resonator is exposed to said second compartment and said second side of said second resonator is exposed to said third compartment.

10. A method for determining chemical composition, the method comprising the steps of:

a first step of exposing a first side of at least one resonator coated with a first sensing film to an analyte and exposing a second side of the at least one resonator coated with a second sensing film to a reference chemical, said first and second sensing films comprising different materials that have respective differentiable affinities toward chemical species of said chemical composition and that are capable of inducing respective differentiable resonant frequencies in said at least one resonator;

a first step of measuring a fundamental frequency of the at least one resonator during the first step of exposing;

a second step of exposing a second side of the at least one resonator to the analyte and exposing the first side of the at least one resonator to the reference chemical;

a second step of measuring the fundamental frequency of the at least one resonator during the second step of exposing; and determining the chemical composition of the analyte based on the first step of measuring and the second step of measuring.

11. A method according to claim 10, wherein said step of determining comprises determining analyte type by comparing results of said first step of measuring and said second step of measuring with normalized resonator responses.

12. A method according to claim 10, wherein said step of determining comprises determining analyte concentration by using multivariate analysis techniques.

13. An apparatus for determining chemical composition, the apparatus comprising:

first means for measuring a fundamental frequency of at least one resonator, a first side of which is coated with a first sensing film and a second side of which is coated with a second sensing film while the first side of the at least one resonator is exposed to an analyte and the second side is exposed to a reference chemical, said first and second sensing films comprising different materials that have respective differentiable affinities toward chemical species of said chemical composition and that are capable of inducing respective differentiable resonant frequencies in said at least one resonator;

second means for measuring the fundamental frequency of the at least one resonator while the second side of the at least one resonator is exposed to the analyte and the first side of the at least one resonator is exposed to the reference chemical; and means for determining chemical composition of the analyte based on results obtained by said first means for measuring and said second means for measuring.

14. An apparatus according to claim 13, wherein said means for determining comprises means for determining analyte type by comparing the results obtained by said first means for measuring and said second means for measuring with normalized resonator responses.

15. An apparatus according to claim 13, wherein said means for determining comprises means for determining analyte concentration by using multivariate analysis techniques.

16. An apparatus according to claim 4, wherein said vessel is divided into at least first and second compartments and wherein a first side of said at least one quartz crystal microbalance resonator is exposed to a first compartment of said vessel, and a second side of said at least one quartz crystal microbalance resonator is exposed to a second compartment of said vessel.

17. An apparatus according to claim 15, wherein said at least one resonator comprises an AT-cut quartz crystal substrate that comprises a first side coated with PIB and a second side coated with an amorphous fluoropolymer.

18. An apparatus according to claim 15, wherein said at least one resonator comprises an AT cut quartz crystal substrate that comprises a first side coated with a hard-soft block elastomer and a second side coated with PECH.

19. An apparatus according to claims 4, further comprising a second quartz crystal microbalance resonator having a first side coated with a third sensing film and a second side coated with a fourth sensing film.

20. An apparatus according to claim 19, wherein said vessel is divided into first, second, and third compartments and said first side of said second quartz crystal microbalance resonator is exposed to said second compartment, and said second side of said second quartz crystal microbalance resonator is exposed to said third compartment.

* * * * *